United States Patent
Beller et al.

(10) Patent No.: US 9,724,331 B2
(45) Date of Patent: Aug. 8, 2017

(54) USE OF MALEIMIDE DERIVATIVES FOR PREVENTING AND TREATING LEUKEMIA

(71) Applicant: CENTOGENE AG, Rostock (DE)

(72) Inventors: Matthias Beller, Nienhagen (DE); Jan Lukas, Rostock (DE); Moritz Frech, Neu Broderstorf (DE); Christian Junghanss, Rostock (DE); Arndt Rolfs, Berlin (DE); Anahit Pews-Davtyan, Rostock (DE); Christian Eisenloeffel, Rostock (DE)

(73) Assignee: Centogene AG, Rostock (DE)

( * ) Notice: Subject to any disclaimer, the term of this patent is extended or adjusted under 35 U.S.C. 154(b) by 0 days.

(21) Appl. No.: 14/650,939

(22) PCT Filed: Dec. 10, 2013

(86) PCT No.: PCT/EP2013/003733
§ 371 (c)(1),
(2) Date: Jun. 10, 2015

(87) PCT Pub. No.: WO2014/090398
PCT Pub. Date: Sep. 16, 2014

(65) Prior Publication Data
US 2015/0306070 A1    Oct. 29, 2015

(30) Foreign Application Priority Data
Dec. 10, 2012   (EP) .................................... 12008229

(51) Int. Cl.
| | |
|---|---|
| A61K 31/404 | (2006.01) |
| A61K 31/203 | (2006.01) |
| A61K 31/44 | (2006.01) |
| A61K 31/675 | (2006.01) |
| A61K 31/704 | (2006.01) |
| A61K 31/7048 | (2006.01) |
| A61K 31/7068 | (2006.01) |
| A61K 31/437 | (2006.01) |
| A61K 31/4439 | (2006.01) |
| A61K 45/06 | (2006.01) |
| C07D 403/04 | (2006.01) |
| C07D 401/14 | (2006.01) |
| C07D 405/04 | (2006.01) |
| C07D 409/14 | (2006.01) |
| C07D 471/04 | (2006.01) |
| C07D 403/14 | (2006.01) |

(52) U.S. Cl.
CPC .......... *A61K 31/404* (2013.01); *A61K 31/203* (2013.01); *A61K 31/437* (2013.01); *A61K 31/44* (2013.01); *A61K 31/4439* (2013.01); *A61K 31/675* (2013.01); *A61K 31/704* (2013.01); *A61K 31/7048* (2013.01); *A61K 31/7068* (2013.01); *A61K 45/06* (2013.01); *C07D 401/14* (2013.01); *C07D 403/04* (2013.01); *C07D 403/14* (2013.01); *C07D 405/04* (2013.01); *C07D 409/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 5,057,614 A | 10/1991 | Davis et al. | |
| 7,405,305 B2 * | 7/2008 | Albaugh | C07D 401/14 546/184 |
| 2006/0009492 A1 * | 1/2006 | Lu | A61K 31/4025 514/320 |

FOREIGN PATENT DOCUMENTS

| | | | |
|---|---|---|---|
| EP | 1057484 A1 | | 12/2000 |
| EP | WO 2009/071620 | * | 6/2009 |
| JP | H03 756935 A | | 3/1991 |
| WO | 02/38561 A1 | | 5/2002 |
| WO | 02/46183 A2 | | 6/2002 |
| WO | 03/103663 A2 | | 12/2003 |

(Continued)

OTHER PUBLICATIONS

Piazza, Francesco. Glycogen Synthase Kincaise-3 regulates multiple myeloma cell growth and bortezomib-induced cell death. BMC Cancer 2010, 10:526, 1-14.*
International Search Report dated May 27, 2014 from PCT International Application No. PCT/EP2013/003733.
Dulsat, C., et al., "MKC-1", Drugs of the Future, vol. 34, No. 4, Jan. 1, 2009, p. 270.
Denny, et al., "MKC-1 is a novel agent that induces cell cycle arrest and disrupts multiple survival pathways in hematologic cancers," AACR 2007, Abst 5611, 2007, 2007, XP002719653, retrieved from the internet: URL:http://www.aacrmeetingabstracts.org/cgi/content/meeting_abstract/2007/1_Annual_Meeting/5611?maxtoshow=

(Continued)

*Primary Examiner* — Samantha Shterengarts
(74) *Attorney, Agent, or Firm* — Ward and Smith, P.A.

(57) ABSTRACT

The present invention is related to a compound of formula (I): a pharmaceutically acceptable salt thereof, a hydrate thereof, a solvate thereof, a metabolite thereof or a prodrug thereof; for use in a method for the treatment and/or prevention of leukemia, wherein X is selected from the group consisting of N—$R^1$, O and S; $R^1$ is selected from the group consisting of alkyl, cycloalkyl, aryl, arylalkyl and hydrogen; $R^2$ is selected from the group consisting of indolyl, substituted indolyl, azaindolyl and substituted azaindolyl; and $R^3$ is selected from the group consisting of aryl, substituted aryl, unsubstituted heteroaryl, heterocyclyl and substituted heterocyclyl.

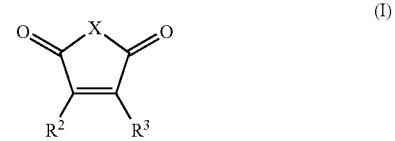

29 Claims, 5 Drawing Sheets

(56) References Cited

FOREIGN PATENT DOCUMENTS

| WO | 2004/072062 A2 | 8/2004 |
|---|---|---|
| WO | 2006/061212 A1 | 6/2006 |
| WO | 2007/008514 A2 | 1/2007 |
| WO | 2009/071620 A1 | 6/2009 |
| WO | 2010/120614 A1 | 10/2010 |

OTHER PUBLICATIONS

&hits=10&RESULTFORMAT=&author1=denny &andorexactfulltext=and&searchid=1&FIRSTINDEX=10 &sortspec=relevance&resourcetype=HWCIT [retrieved on Feb. 13, 2014].
Song, E. Y., et al., "Glycogen synthase kinase-3beta inhibitors suppress leukemia cell growth," Experimental Hematology, Elsevier Inc., Us, vol. 38, No. 10, Oct. 1, 2010, pp. 908-921.
Pews-Davtyan, Anahit, et al., "Efficient palladium-catalyzed synthesis of 3-aryl-4-indolylmaleimides," Organic & Biomolecular Chemistry, vol. 6, No. 6, Jan. 1, 2008, p. 992.
Schmole, A. C., et al., "Novel indolymaleimide acts as GSK-3beta inhibitor in human neural progenitor cells," Bio-Organic & Medicinal Chemistry, Pergamon, GB, vol. 18, No. 18, Sep. 15, 2010, pp. 6785-6795.
Katoh, M., et al., "Structure-activity relationship of N-methyl-bisindolylmaleimide derivatives as cell death inhibitors," Bio-Organic & Medicinal Chemistry Letters, Pergamon, Amsterdam, NL, vol. 15, No. 12, Jun. 15, 2005, pp. 3109-3113.
Xu, G-Q, et al., "Synthesis and cytotoxicity of indolopyrrolemaleimides," Chemical and Pharmaceutical Bulletin, Pharmaceutical Society of Japan, JP, vol. 55, No. 9, Sep. 1, 2007, pp. 1302-1307.
Davis, Peter D., et al., "Inhibitors of protein kinase C. 1. 2,3-bisarylmaleimides," Journal of Medicinal Chemistry, American Chemical Society, US, vol. 35, No. 1, Jan. 1, 1992, pp. 177-184.
Eisenloffel, Christian, et al., "Interference of a novel indolylmaleimide with microtubules induces mitotic arrest and apoptosis in human progenitor and cancer cells," Biochemical Pharmacology, vol. 85, No. 6, Mar. 1, 2013, pp. 763-771.
Garaeva, L. D., "The synthesis and cytotoxic activity of D-ribofuranosides and 2-deoxy-D-ribofuranosides of substituted bis(indolyl)furan, bis(indolyl)pyrrole, and indolo[2,3-a]carbazole derivatives," Russian Journal of Bio-Organic Chemistry, vol. 29, No. 2, Jan. 1, 2003, pp. 160-167.
Grewal, Baljinder K., et al., "Theoretical investigations on maleimide and its indolyl derivatives: Rational drug design approach for PKC[beta]II inhibitors," Journal of Molecular Structure, Vo. 1029, Dec. 1, 2012, pp. 35-44.
Shorunov, S. V., et al., "A convenient synthesis of 3,4diaryl(hetaryl)-substituted maleimides and maleic anhydrides," Russian Journal of Organic Chemistry, Nauka/Interperiodica, Mo, vol. 42, No. 10, Oct. 1, 2006, pp. 1490-1497.

* cited by examiner

| IC50 [μM] | 48 h | 72 h |
|---|---|---|
| SEM | 0.85 | 0.41 |
| RS4;11 | 2.14 | 0.74 |
| Jurkat | 2.32 | 1.28 |
| Molt-4 | 2.41 | 0.52 |

USE OF MALEIMIDE DERIVATIVES FOR PREVENTING AND TREATING LEUKEMIA

CROSS-REFERENCE TO RELATED APPLICATIONS

This application is a 35 U.S.C. §371 National Stage Entry of International Application No. PCT/EP2013/003733 having an international filing date of Dec. 10, 2013, which claims the benefit of European Application No. EP 12 008 229.2 filed Dec. 10, 2012, the content of which is herein incorporated by reference in its entirety.

The present invention relates to a chemical compound of formula (I), its use in the treatment of a disease, a pharmaceutical composition comprising the compound, and a method for the treatment of a disease.

Leukemia is a malignant cancer of the bone marrow and blood and characterized by the uncontrolled growth of blood cells. The common types of leukemia are divided into four categories: acute or chronic myelogenous, involving the myeloid elements of the bone marrow, and acute or chronic lymphocytic, involving the cells of the lymphoid lineage. In general, acute leukemia, unlike the chronic form, is potentially curable. Standard treatment for leukemia usually involves chemotherapy and/or stem cell transplantation and/or radiation therapy.

Chemotherapy in leukemia usually involves a combination of two or more chemotherapeutic agents. Some common combinations include cytarabine with either doxorubicin or daunorubicin or mitoxantrone or thioguanine, mercaptopurine with methotrexate, mitroxantrone with etoposide, asparaginase with vincristine, daunorubicin and prednisone, cyclophosphamide with vincristine, cytarabine and prednisone, cyclophosphamide with vincristine and prednisone, daunorubicin with cytarabine and thioguanine, and daunorubicin with vincristine and prednisone.

Treatment of leukemia is very complex and depends on its type. Despite improvements in outcome with current treatment programs, the need to discover novel agents for the treatment of all types of leukemia continues.

The investigation of signal transduction pathways and the development of specific agents are important factors to further improve the therapy of leukemia. Different studies of acute leukemia showed that aberrant signaling of phosphatidylinositol 3-kinase (PI3K)/AKT promotes cell transformation and malignant progression (Martelli et al. Biochim Biophys Acta 2010, 1803, 991-1002; Park et al., Haematologica 2010, 95, 819-28; Gutierrez et al. Blood 2009, 114, 647-50). Glycogen Synthase Kinase 3β (GSK3β) is a substrate of protein kinase Akt and important for metabolic function. GSK3β is a serine/threonine kinase which is highly activated in resting cells (Kockeritz et al., Current drug targets, 2009, 7, 1377-88). Aside from its influence on the glycogen synthesis GSK3β is involved in the Wnt/β-catenin pathway. In the Wnt/β-catenin pathway, GSK3β is part of the destruction complex of β-catenin and prevents its translocation into the nucleus. Therefore the transcription of genes which are involved in proliferation, differentiation and the embryonic development are inhibited (Logan et al., Annual review of cell and developmental biology 2004, 20, 781-810). In the PI3K/Akt signaling pathway GSK3β is phosphorylated by Akt and thus inactivated. Thereby, the phosphorylation of GSK3β targets is inhibited (Vivanco, I. and Sawyers, C. L., Nature reviews. Cancer, 2, 489-501.

Hence, in both pathways GSK3β antagonizes cell growth and cell cycle progression. In accordance therewith, the inhibition of GSK3β led to decreased cell growth and increased apoptosis in different tumor cell types, namely glioblastoma cells (Korur et al., PloS one, 4, e7443), gastrointestinal cancer cells (Mai et al., Clinical cancer research 2009, 5, 6810-9; Ghosh Clinical cancer research 2009, 11, 4580-8), ovarian cancer cells (Cao et al. Cell research 2009, 16, 671-7), medullary thyroid cancer cells (Kunnimalaiyaan, M et al., Molecular cancer therapeutics 2007, 6, 1151), pancreatic cancer cells (Ougolkov et al., Cancer research 2005, 65, 2076-81) and leukemia cells (Hu et al., Journal of experimental clinical cancer research 2010, 29, 154).

The problem underlying the present invention is the provision of a means suitable for the treatment of leukemia. A further problem underlying the present invention is the provision of a pharmaceutical composition suitable for the treatment of leukemia. A still further problem underlying the present invention is the provision of a method for the treatment of leukemia.

The problem underlying the present invention is solved by the subject matter of the attached independent claims, preferred embodiments may be taken from the attached dependent claims. Further aspects of the invention and various embodiments thereof are disclosed in the following.

Embodiment 1

A compound of formula (I):

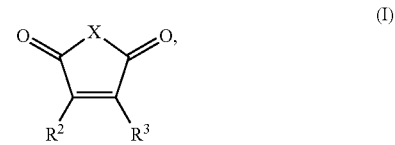

a pharmaceutically acceptable salt thereof, a hydrate thereof, a solvate thereof, a metabolite thereof or a prodrug thereof;

for use in a method for the treatment and/or prevention of leukemia, wherein

X is selected from the group consisting of N—$R^1$, O and S;

$R^1$ is selected from the group consisting of alkyl, cycloalkyl, aryl, arylalkyl and hydrogen;

$R^2$ is selected from the group consisting of indolyl, substituted indolyl, azaindolyl and substituted azaindolyl; and $R^3$ is selected from the group consisting of aryl, substituted aryl, unsubstituted heteroaryl, heterocyclyl and substituted heterocyclyl.

Embodiment 2

The compound of embodiment 1, wherein $R^2$ comprises one, two, three, four, five or six substituents, whereby each and any of the substituents is individually and independently selected from the group comprising halogen, alkyl, alkenyl, alkynyl, acyl, formyl, cycloalkyl, aryl, haloalkyl, polyfluoroalkyl, alkylthio, arylthio, monoalkylamino, dialkylamino, monoarylamino, diarylamino, alkylarylamino, alkylimido, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido.

Embodiment 3

The compound of any one of embodiments 1 to 2, wherein $R^3$ comprises one, two, three, four, five, six or seven substituents, whereby each and any of the substituents is individually and independently selected from the group comprising hydrogen, alkyl, alkenyl, alkynyl, aryl, acyl, formyl, halogen, haloalkyl, alkylthio, monoalkylamino, dialkylamino, monoarylamino, diarylamino, alkylarylamino, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido.

Embodiment 4

The compound of any one of embodiments 1 to 3, wherein X is N—$R^1$, and wherein
$R^1$ is preferably selected from the group consisting of alkyl, hydrogen, phenyl and benzyl.

Embodiment 5

The compound of embodiment 4, wherein
$R^1$ is selected from the group consisting of methyl, butyl and hydrogen, preferably $R^1$ is selected from the group consisting of methyl and hydrogen.

Embodiment 6

The compound of any one of embodiments 1 to 3, wherein X is O.

Embodiment 7

The compound of any one of embodiments 1 to 6, preferably any one of embodiments 4 to 6, wherein
$R^3$ is selected from the group consisting of monocyclic aryl, substituted monocyclic aryl, bicyclic aryl, substituted bicyclic aryl, monocyclic heteroaryl, substituted monocyclic heteroaryl, bicyclic heteroaryl and substituted bicyclic heteroaryl.

Embodiment 8

The compound of embodiment 7, wherein
$R^3$ is selected from the group consisting of phenyl, substituted phenyl, naphthenyl, substituted naphthenyl, heteroaryl with 5, 6, 9 or 10 ring atoms and substituted heteroaryl with 5, 6, 9 or 10 atoms, wherein heteroaryl contains 1 or 2 heteroatoms, wherein each and any of the heteroatoms is selected from the group consisting of N, O and S, wherein preferably heteroaryl is selected from the group consisting of indolyl, thiophenyl and pyridinyl, and substituted heteroaryl is selected from the group consisting of substituted indolyl, substituted thiophenyl and substituted pyridinyl.

Embodiment 9

The compound of embodiment 8, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 10

The compound of embodiment 9, wherein
$R^3$ is selected from the group consisting of phenyl and substituted phenyl, wherein substituted phenyl is phenyl consisting of one, two or three substituents, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 11

The compound of embodiment 8, wherein $R^3$ is substituted phenyl and each and any of the substituents is individually any independently selected from the group consisting of alkyl, substituted alkyl, alkoxy, substituted alkoxy, alkynly and halogen.

Embodiment 12

The compound of embodiment 11, wherein
alkyl is methyl or ethyl,
substituted alkyl is halogen-substituted methyl or acetyl,
alkoxy is ethoxy, and
alkynyl is vinyl.

Embodiment 13

The compound of embodiment 8, wherein the compound is of formula (IV)

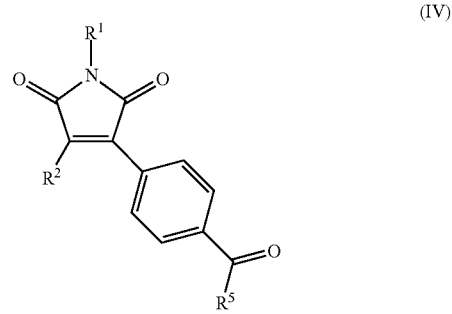

(IV)

wherein $R^5$ is selected from the group consisting of alkyl, aminoalkyl, alkoxyalkyl, hydroxyalkyl, aryl and heteroaryl.

Embodiment 14

The compound of embodiment 13, wherein
$R^5$ is methyl.

Embodiment 15

The compound of any of embodiments 1 to 14, preferably any one of embodiments 1 to 6, more preferably any one of embodiments 4 to 6, wherein each and any of indolyl, substituted indolyl, azaindolyl and substituted azaindolyl of $R^2$ is individually and independently either unprotected or protected at N, preferably at N of the 5-membered ring.

Embodiment 16

The compound of any one of embodiments 1 to 15, preferably any one of embodiments 1 to 6, more preferably any one of embodiments 4 to 6, wherein $R^2$ is a moiety of formula (VIa)

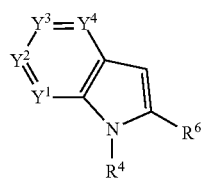

wherein
$R^4$ is selected from the group consisting of hydrogen, aryl, heteroaryl, alkyl, cycloalkyl, polyfluoroalkyl, arylalkyl and heteroarylalkyl,
$R^6$ is selected from the group consisting of alkyl and aryl, each and any of $Y^1$, $Y^2$, $Y^3$ and $Y^4$ is individually and independently selected from the group consisting of N and $CR^7$, under the proviso that at least two of $Y^1$, $Y^2$, $Y^3$ and $Y^4$ are $CR^7$,
wherein
each and any of $R^7$ is individually and independently selected from the group consisting of hydrogen, halogen, alkyl, alkenyl, alkynyl, acyl, formyl, cycloalkyl, aryl, haloalkyl, polyfluoroalkyl, alkylthio, arylthio, monoalkylamino, dialkylamino, monoarylamino, diarylamino, alkylarylamino, alkylimido, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido, preferably each and any of $R^7$ is individually and independently selected from the group consisting of methyl and methoxy, more preferably $R^7$ is 5-methoxy or 5-halogen.

Embodiment 17

The compound of embodiment 16, wherein each and any of $Y^1$, $Y^2$, $Y^3$ and $Y^4$ is $CR^7$.

Embodiment 18

The compound of embodiment 17, wherein $R^7$ is hydrogen.

Embodiment 19

The compound of any one of embodiments 16 to 18, preferably of any one of embodiments 17 to 18, wherein $R^4$ is selected from the group consisting of hydrogen, alkyl and benzyl, preferably $R^4$ is hydrogen or methyl, more preferably $R^4$ is hydrogen.

Embodiment 20

The compound of any one of embodiments 16 to 19, preferably any one of embodiments 17 to 19, wherein R6 is hydrogen or alkyl, preferably hydrogen or methyl, more preferably methyl.

Embodiment 21

The compound of embodiment 16, wherein each and any of $Y^1$, $Y^2$, $Y^3$ and $Y^4$ is individually and independently selected from the group consisting of N and $CR^7$, under the proviso that one or two of $Y^1$, $Y^2$, $Y^3$ and $Y^4$ are N.

Embodiment 22

The compound of embodiment 21, wherein $R^7$ is hydrogen.

Embodiment 23

The compound of any one of embodiments 16 and 21 to 22, preferably of any one of embodiments 21 to 22, wherein $R^4$ is selected from the group consisting of hydrogen, alkyl and benzyl, preferably $R^4$ is hydrogen or methyl, more preferably $R^4$ is hydrogen.

Embodiment 24

The compound of any one of embodiments 16 and 21 to 23, preferably any one of embodiments 21 to 23, wherein $R^6$ is hydrogen or alkyl, preferably hydrogen or methyl, more preferably methyl.

Embodiment 25

The compound of any one of embodiments 1 to 24, preferably any one of embodiments 16 to 24, wherein $R^3$ is selected from the group consisting of monocyclic aryl, substituted monocyclic aryl, bicyclic aryl, substituted bicyclic aryl, monocyclic heteroaryl, substituted monocyclic heteroaryl, bicyclic heteroaryl and substituted bicyclic heteroaryl.

Embodiment 26

The compound of embodiment 25, wherein $R^3$ is selected from the group consisting of phenyl, substituted phenyl, naphthenyl, substituted naphthenyl, heteroaryl with 5, 6, 9 or 10 ring atoms and substituted heteroaryl with 5, 6, 9 or 10 ring atoms, wherein heteroaryl contains 1 or 2 heteroatoms, wherein each and any of the heteroatoms is selected from the group consisting of N, O and S, wherein preferably heteroaryl is selected from the group consisting of indolyl, thiophenyl and pyridinyl, and substituted heteroaryl is selected from the group consisting of substituted phenyl, substituted thiophenyl and substituted pyridinyl.

Embodiment 27

The compound of embodiment 26, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 28

The compound of embodiment 27, wherein $R^3$ is selected from the group consisting of phenyl and substituted phenyl, wherein substituted phenyl is phenyl consisting of one, two or three substituents, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 29

The compound of embodiment 26, wherein each and any of the substituents is individually any independently selected from the group consisting of alkyl, substituted alkyl, alkoxy, substituted alkoxy, alkynly and halogen.

Embodiment 30

The compound of embodiment 29, wherein
alkyl is methyl or ethyl,
substituted alkyl is halogen-substituted methyl or acetyl,
alkoxy is ethoxy, and
alkynyl is vinyl.

Embodiment 31

The compound of any one of embodiments 16 to 26, preferably embodiment 26, wherein the compound is of formula (VI)

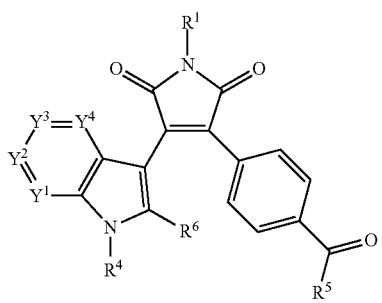

(VI)

wherein $R^5$ is selected from the group consisting of alkyl, aminoalkyl, alkoxyalkyl, hydroxyalkyl, aryl and heteroaryl.

Embodiment 32

The compound of any one of embodiments 16 to 26, preferably embodiment 26, wherein the compound is of formula (V)

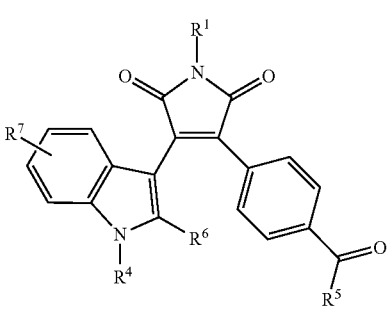

(V)

Embodiment 33

The compound of any one of embodiments 31 and 32, wherein
$R^5$ is methyl.

Embodiment 34

The compound of any one of embodiments 1 to 33, wherein the compound is selected from the group consisting of 1-Methyl-3,4-bis-(2-methyl-1H-indol-3-yl)-1H-pyrrole-2,5-dione; 1-Methyl-3-(2-methyl-1H-indol-3-yl)-4-(4-vinylphenyl)-1H-pyrrole-2,5-dione; 1-Methyl-3-(2-methyl-1H-indol-3-yl)-4-phenyl-1H-pyrrole-2,5-dione; 3-(4-Acetylphenyl)-1-methyl-4-(2-methyl-1H-indol-3-yl)-1H-pyrrole-2,5-dione (also referred to herein as PDA-66); 3-(2,6-Dimethylphenyl)-1-methyl-4-(2-methyl-1H-indol-3-yl)-1H-pyrrole-2,5-dione; 3-(3-Chlorophenyl)-1-methyl-4-(2-methyl-1H-indol-3-yl)-1H-pyrrole-2,5-dione; 3-(2,4-Dichlorophenyl)-1-methyl-4-(2-methyl-1H-indol-3-yl)-1H-pyrrole-2,5-dione; 1-Methyl-3-(2-methyl-1H-indol-3-yl)-4-(thiophen-3-yl)-1H-pyrrole-2,5-dione; 1-Methyl-3-(2-methyl-1H-indol-3-yl)-4-(pyridin-4-yl)-1H-pyrrole-2,5-dione; 1-Methyl-3-(2-methyl-1H-indol-3-yl)-4-(naphthalen-2-yl)-1H-pyrrole-2,5-dione; 3-(2,5-Dimethoxyphenyl)-1-methyl-4-(2-methyl-1H-indol-3-yl)-1H-pyrrole-2,5-dione; 1-Methyl-3-(2-methyl-1H-indol-3-yl)-4-(2-(trifluoromethyl)phenyl)-1H-pyrrole-2,5-dione; 3-(4-Fluorophenyl)-1-methyl-4-(2-methyl-1H-indol-3-yl)-1H-pyrrole-2,5-dione; 3-(5-Acetyl-2-fluorophenyl)-1-methyl-4-(2-methyl-1H-indol-3-yl)-1H-pyrrole-2,5-dione; N-(4-(1-Methyl-4-(2-methyl-1H-indol-3-yl)-2,5-dioxo-2,5-dihydro-1H-pyrrol-3-yl)phenyl) acetamide; 3-(2-Methyl-1H-indol-3-yl)-4-phenylfuran-2,5-dione; 3-(4-Acetylphenyl)-4-(2-methyl-1H-indol-3-yl)-1H-pyrrole-2,5-dione; 3-(2-Methyl-1H-indol-3-yl)-4-(naphthalen-2-yl)furan-2,5-dione; 3-(2-Methyl-1H-indol-3-yl)-4-(naphthalen-2-yl)-1H-pyrrole-2,5-dione; 3-(4-Acetylphenyl)-4-(2-methyl-1H-indol-3-yl)furan-2,5-dione; and 3-(2-Methyl-1H-indol-3-yl)-4-phenyl-1H-pyrrole-2,5-dione Embodiment 35

The compound of any one of embodiments 1 to 34, wherein the compound is 3-(4-acetylphenyl)-4-(2-methyl-1H-indol-3-yl)-1H-pyrrole-2,5-dione

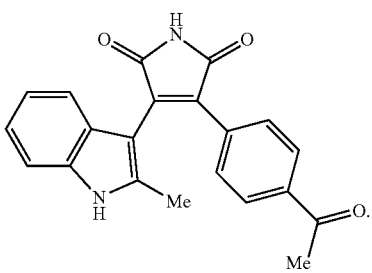

(VII)

Embodiment 36

The compound of any one of embodiments 1 to 34, wherein the compound is 3-(4-acetylphenyl)-1-methyl-4-(2-methyl-1H-indol-3-yl)-1H-pyrrole-2,5-dione

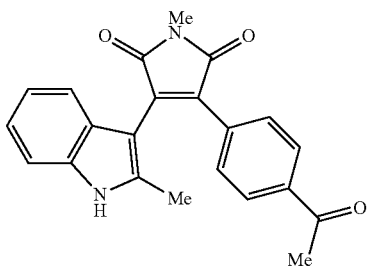

Embodiment 37

A compound of formula (I):

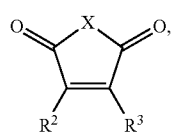

(I)

a pharmaceutically acceptable salt thereof, a hydrate thereof, a solvate thereof, a metabolite thereof or a prodrug thereof; wherein
X is selected from the group consisting of N—$R^1$, O and S;
$R^1$ is selected from the group consisting of alkyl, cycloalkyl, aryl, arylalkyl and hydrogen;
$R^2$ is selected from the group consisting of indolyl, substituted indolyl, azaindolyl and substituted azaindolyl; and
$R^3$ is selected from the group consisting of aryl, substituted aryl, unsubstituted heteroaryl, heterocyclyl and substituted heterocyclyl.

Embodiment 38

The compound of embodiment 37, wherein
$R^2$ comprises one, two, three, four, five or six substituents, whereby each and any of the substituents is individually and independently selected from the group comprising halogen, alkyl, alkenyl, alkynyl, acyl, formyl, cycloalkyl, aryl, haloalkyl, polyfluoroalkyl, alkylthio, arylthio, monoalkylamino, dialkylamino, monoarylamino, diarylamino, alkylarylamino, alkylimido, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido.

Embodiment 39

The compound of any one of embodiments 37 to 38, wherein
$R^3$ comprises one, two, three, four, five, six or seven substituents, whereby each and any of the substituents is individually and independently selected from the group comprising hydrogen, alkyl, alkenyl, alkynyl, aryl, acyl, formyl, halogen, haloalkyl, alkylthio, monoalkylamino, dialkylamino, monoarylamino, diarylamino, alkylarylamino, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido.

Embodiment 40

The compound of any one of embodiments 37-39, wherein
X is N—$R^1$, and wherein
$R^1$ is preferably selected from the group consisting of alkyl, hydrogen, phenyl and benzyl.

Embodiment 41

The compound of embodiment 40, wherein
$R^1$ is selected from the group consisting of methyl, butyl and hydrogen, preferably $R^1$ is selected from the group consisting of methyl and hydrogen.

Embodiment 42

The compound of any one of embodiments 37 to 39, wherein X is O.

Embodiment 43

The compound of any one of embodiments 37 to 42, preferably any one of embodiments 4 to 6, wherein
$R^3$ is selected from the group consisting of monocyclic aryl, substituted monocyclic aryl, bicyclic aryl, substituted bicyclic aryl, monocyclic heteroaryl, substituted monocyclic heteroaryl, bicyclic heteroaryl and substituted bicyclic heteroaryl.

Embodiment 44

The compound of embodiment 43, wherein
$R^3$ is selected from the group consisting of phenyl, substituted phenyl, naphthenyl, substituted naphthenyl, heteroaryl with 5, 6, 9 or 10 ring atoms and substituted heteroaryl with 5, 6, 9 or 10 atoms, wherein heteroaryl contains 1 or 2 heteroatoms, wherein each and any of the heteroatoms is selected from the group consisting of N, O and S, wherein preferably heteroaryl is selected from the group consisting of indolyl, thiophenyl and pyridinyl, and substituted heteroaryl is selected from the group consisting of substituted indolyl, substituted thiophenyl and substituted pyridinyl.

Embodiment 45

The compound of embodiment 44, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 46

The compound of embodiment 45, wherein
$R^3$ is selected from the group consisting of phenyl and substituted phenyl, wherein substituted phenyl is phenyl consisting of one, two or three substituents, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 47

The compound of embodiment 44, wherein $R^3$ is substituted phenyl and each and any of the substituents is individually any independently selected from the group consisting of alkyl, substituted alkyl, alkoxy, substituted alkoxy, alkynly and halogen.

Embodiment 48

The compound of embodiment 47, wherein
alkyl is methyl or ethyl,
substituted alkyl is halogen-substituted methyl or acetyl,
alkoxy is ethoxy, and
alkynyl is vinyl.

Embodiment 49

The compound of embodiment 44, wherein the compound is of formula (IV)

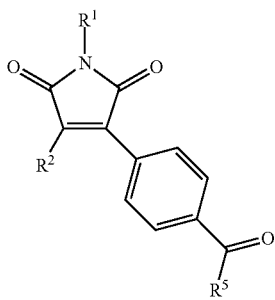

(IV)

wherein $R^5$ is selected from the group consisting of alkyl, aminoalkyl, alkoxyalkyl, hydroxyalkyl, aryl and heteroaryl.

Embodiment 50

The compound of embodiment 49, wherein
$R^5$ is methyl.

Embodiment 51

The compound of any of embodiments 37 to 50, preferably any one of embodiments 1 to 6, more preferably any one of embodiments 4 to 6, wherein each and any of indolyl, substituted indolyl, azaindolyl and substituted azaindolyl of $R^2$ is individually and independently either unprotected or protected at N, preferably at N of the 5-membered ring.

Embodiment 52

The compound of any one of embodiments 37 to 51, preferably any one of embodiments 37 to 42, more preferably any one of embodiments 40 to 42, wherein $R^2$ is a moiety of formula (VIa)

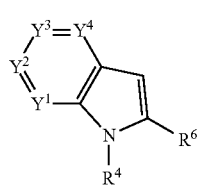

(VIa)

wherein
$R^4$ is selected from the group consisting of hydrogen, aryl, heteroaryl, alkyl, cycloalkyl, polyfluoroalkyl, arylalkyl and heteroarylalkyl,
$R^6$ is selected from the group consisting of alkyl and aryl, each and any of $Y^1$, $Y^2$, $Y^3$ and $Y^4$ is individually and independently selected from the group consisting of N and $CR^7$, under the proviso that at least two of $Y^1$, $Y^2$, $Y^3$ and $Y^4$ are $CR^7$,
wherein
each and any of $R^7$ is individually and independently selected from the group consisting of hydrogen, halogen, alkyl, alkenyl, alkynyl, acyl, formyl, cycloalkyl, aryl, haloalkyl, polyfluoroalkyl, alkylthio, arylthio, monoalkylamino, dialkylamino, monoarylamino, diarylamino, alkylarylamino, alkylimido, hydroxy, alkoxy, aryloxy, carboxyl, alkoxycarbonyl, aryloxycarbonyl, cyano, amino, amido, acylamino, nitro, alkylsulfinyl, arylsulfinyl, alkylsulfonyl, arylsulfonyl, alkylsulfinamido, arylsulfinamido, alkylsulfonamido and arylsulfonamido, preferably each and any of $R^7$ is individually and independently selected from the group consisting of methyl and methoxy, more preferably $R^7$ is 5-methoxy or 5-halogen.

Embodiment 53

The compound of embodiment 52, wherein
each and any of $Y^1$, $Y^2$, $Y^3$ and $Y^4$ is $CR^7$.

Embodiment 54

The compound of embodiment 53, wherein
$R^7$ is hydrogen.

Embodiment 55

The compound of any one of embodiments 52 to 54, preferably of any one of embodiments 53 to 54, wherein $R^4$ is selected from the group consisting of hydrogen, alkyl and benzyl, preferably $R^4$ is hydrogen or methyl, more preferably $R^4$ is hydrogen.

Embodiment 56

The compound of any one of embodiments 52 to 55, preferably any one of embodiments 53 to 55, wherein R6 is hydrogen or alkyl, preferably hydrogen or methyl, more preferably methyl.

Embodiment 57

The compound of embodiment 52, wherein
each and any of $Y^1$, $Y^2$, $Y^3$ and $Y^4$ is individually and independently selected from the group consisting of N and $CR^7$, under the proviso that one or two of $Y^1$, $Y^2$, $Y^3$ and $Y^4$ are N.

Embodiment 58

The compound of embodiment 57, wherein
$R^7$ is hydrogen.

Embodiment 59

The compound of any one of embodiments 52 and 57 to 58, preferably of any one of embodiments 57 to 58, wherein $R^4$ is selected from the group consisting of hydrogen, alkyl and benzyl, preferably $R^4$ is hydrogen or methyl, more preferably $R^4$ is hydrogen.

Embodiment 60

The compound of any one of embodiments 52 and 57 to 59, preferably any one of embodiments 57 to 59, wherein $R^6$ is hydrogen or alkyl, preferably hydrogen or methyl, more preferably methyl.

Embodiment 61

The compound of any one of embodiments 37 to 60, preferably any one of embodiments 52 to 60, wherein $R^3$ is selected from the group consisting of monocyclic aryl, substituted monocyclic aryl, bicyclic aryl, substituted bicyclic aryl, monocyclic heteroaryl, substituted monocyclic heteroaryl, bicyclic heteroaryl and substituted bicyclic heteroaryl.

Embodiment 62

The compound of embodiment 61, wherein
$R^3$ is selected from the group consisting of phenyl, substituted phenyl, naphthenyl, substituted naphthenyl, heteroaryl with 5, 6, 9 or 10 ring atoms and substituted heteroaryl with 5, 6, 9 or 10 ring atoms, wherein heteroaryl contains 1 or 2 heteroatoms, wherein each and any of the heteroatoms is selected from the group consisting of N, O and S, wherein preferably heteroaryl is selected from the group consisting of indolyl, thiophenyl and pyridinyl, and substituted heteroaryl is selected from the group consisting of substituted phenyl, substituted thiophenyl and substituted pyridinyl.

Embodiment 63

The compound of embodiment 62, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 64

The compound of embodiment 63, wherein
$R^3$ is selected from the group consisting of phenyl and substituted phenyl, wherein substituted phenyl is phenyl consisting of one, two or three substituents, wherein each and any of the substituents is individually and independently selected from the group consisting of fluoro, chloro, methyl, trifluoromethyl, vinyl, acetyl, acetamido, methoxy, formyl, ethoxycarbonyl and ydimethylamidocarbonyl.

Embodiment 65

The compound of embodiment 62, wherein each and any of the substituents is individually any independently selected from the group consisting of alkyl, substituted alkyl, alkoxy, substituted alkoxy, alkynly and halogen.

Embodiment 66

The compound of embodiment 65, wherein
alkyl is methyl or ethyl,
substituted alkyl is halogen-substituted methyl or acetyl,
alkoxy is ethoxy, and
alkynyl is vinyl.

Embodiment 67

The compound of any one of embodiments 52 to 62, preferably embodiment 62, wherein the compound is of formula (VI)

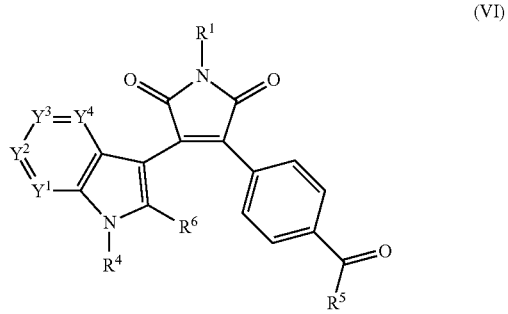

(VI)

wherein $R^5$ is selected from the group consisting of alkyl, aminoalkyl, alkoxyalkyl, hydroxyalkyl, aryl and heteroaryl.

Embodiment 68

The compound of any one of embodiments 52 to 62, preferably embodiment 62, wherein the compound is of formula (V)

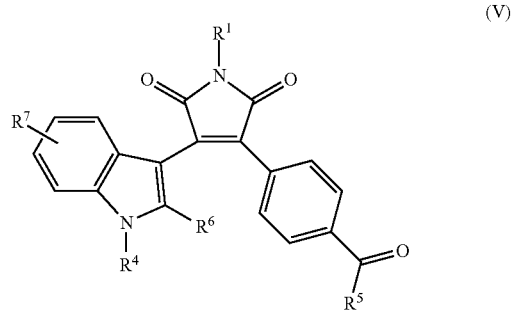

(V)

Embodiment 69

The compound of any one of embodiments 67 and 68, wherein
$R^5$ is methyl.

Embodiment 70

The compound of any one of embodiments 37 to 69, wherein the compound is selected from the group consisting of 1-Methyl-3,4-bis-(2-methyl-1H-indol-3-yl)-1H-pyrrole-2,5-dione; 1-Methyl-3-(2-methyl-1H-indol-3-yl)-4-(4-vinylphenyl)-1H-pyrrole-2,5-dione; 1-Methyl-3-(2-methyl-1H-indol-3-yl)-4-phenyl-1H-pyrrole-2,5-dione; 3-(4-Acetylphenyl)-1-methyl-4-(2-methyl-1H-indol-3-yl)-1H-pyrrole-2,5-dione (also referred to herein as PDA-66); 3-(2,6-Dimethylphenyl)-1-methyl-4-(2-methyl-1H-indol-3-yl)-1H-pyrrole-2,5-dione; 3-(3-Chlorophenyl)-1-methyl-4-(2-methyl-1H-indol-3-yl)-1H-pyrrole-2,5-dione; 3-(2,4-Dichlorophenyl)-1-methyl-4-(2-methyl-1H-indol-3-yl)-1H- pyrrole-2,5-dione; 1-Methyl-3-(2-methyl-1H-indol-3-yl)-4-(thiophen-3-yl)-1H-pyrrole-2,5-dione; 1-Methyl-3-(2-methyl-1H-indol-3-yl)-4-(pyridin-4-yl)-1H-pyrrole-2,5-dione; 1-Methyl-3-(2-methyl-1H-indol-3-yl)-4-(naphthalen-2-yl)-1H-pyrrole-2,5-dione; 3-(2,5-Dimethoxyphenyl)-1-methyl-4-(2-methyl-1H-indol-3-yl)-1H-pyrrole-2,5-dione; 1-Methyl-3-(2-methyl-1H-indol-3-yl)-4-(2-(trifluoromethyl)phenyl)-1H-pyrrole-2,5-dione; 3-(4-Fluorophenyl)-1-methyl-4-(2-methyl-1H-indol-3-yl)-1H-pyrrole-2,5-dione; 3-(5-Acetyl-2-fluorophenyl)-1-methyl-4-(2-methyl-1H-indol-3-yl)-1H-pyrrole-2,5-dione; N-(4-(1-Methyl-4-(2-methyl-1H-indol-3-yl)-2,5-dioxo-2,5-dihydro-1H-pyrrol-3-yl)phenyl) acetamide; 3-(2-Methyl-1H-indol-3-yl)-4-phenylfuran-2,5-dione; 3-(4-Acetylphenyl)-4-(2-methyl-1H-indol-3-yl)-1H-pyrrole-2,5-dione; 3-(2-Methyl-1H-indol-3-yl)-4-(naphthalen-2-yl)furan-2,5-dione; 3-(2-Methyl-1H-indol-3-yl)-4-(naphthalen-2-yl)-1H-pyrrole-2,5-dione; 3-(4-Acetylphenyl)-4-(2-methyl-1H-indol-3-yl)furan-2,5-dione; and 3-(2-Methyl-1H-indol-3-yl)-4-phenyl-1H-pyrrole-2,5-dione Embodiment 71

The compound of any one of embodiments 37 to 70, wherein the compound is 3-(4-acetylphenyl)-4-(2-methyl-1H-indol-3-yl)-1H-pyrrole-2,5-dione

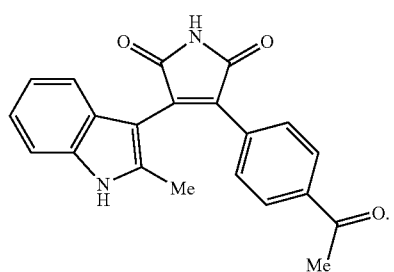

(VII)

Embodiment 72

The compound of any one of embodiments 37 to 70, wherein the compound is 3-(4-acetylphenyl)-1-methyl-4-(2-methyl-1H-indol-3-yl)-1H-pyrrole-2,5-dione

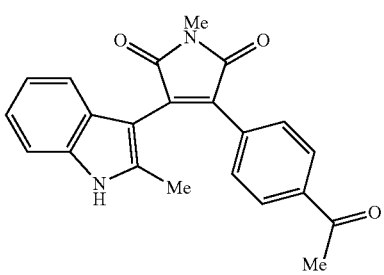

(VIII)

Embodiment 73

The compound of any one of embodiments 37 to 72, wherein R3 is different from indolyl and/or substituted indolyl.

Embodiment 74

The compound of any one of embodiments 1 to 36, wherein leukemia is ALL.

Embodiment 75

The compound of any one of embodiments 1 to 36, wherein leukemia is AML.

Embodiment 76

The compound of any one of embodiments 1 to 36, wherein leukemia is refractory leukemia.

Embodiment 77

The compound of any one of embodiments 1 to 36, wherein leukemia is resistant leukemia.

Embodiment 78

The compound of any one of embodiments 1 to 36, wherein leukemia is FLT3-ITD-positive leukemia.

Embodiment 79

The compound of any one of embodiments 1 to 36, wherein leukemia is any chronic leukemia Embodiment 80

The compound of any one of embodiments 1 to 36, wherein leukemia is myelodysplasia.

Embodiment 81

The compound of any one of embodiments 1 to 36, wherein leukemia is lymphoma.

Embodiment 82

The compound of any one of embodiments 1 to 36 and 74 to 81, wherein the method comprises the administration of a second therapeutic agent, wherein the second therapeutic agent is a chemotherapeutic agent.

Embodiment 83

The compound of embodiment 82, wherein the chemotherapeutic agent is selected from the group comprising cytarabine, etoposide, mitoxantron, cyclophosphamide, retinoic acid, daunorubicin, doxorubicin, idarubicin, azacytidine, decitabine, a tyrosin-kinase inhibitor, a antineoplastic antibody, vincaalkaloids and steroids.

Embodiment 84

The compound of embodiment 83, wherein the chemotherapeutic agent is a tyrosin-kinas inhibitor, wherein the tyrosin-kinase inhibitor is selected from the group comprising sorafenib, dasatinib, nilotinib, nelarabine and fludarabine.

Embodiment 85

The compound of embodiment 83, wherein the chemotherapeutic agent is Alemtuzumab (Campath®)

Embodiment 86

Use of compounds according to any one of embodiments 1 to 73 for the manufacture of a medicament against leukemia.

Embodiment 87

A pharmaceutical compositions comprising a compound of any one of embodiments 1 to 73 and a pharmaceutically acceptable carrier or excipient.

Embodiment 88

The pharmaceutical composition of embodiment 87, wherein the pharmaceutical composition comprises a second therapeutic agent, wherein the second therapeutic agent is a chemotherapeutic agent.

Embodiment 89

A method of treatment and/or prevention of leukemia, wherein the method comprises administering to a subject in need thereof a therapeutically effective amount of a compound of any one of embodiments 1 to 73 or of a pharmaceutical composition of any one of embodiments 87 to 88.

The present invention is based on the surprising finding that that the compound of the invention is capable of inhibition GSK3β. More specifically, the present invention is based on the surprising finding that the compound of the invention is suitable for the treatment of leukemia.

In an embodiment of the compound of the invention the indolyl, substituted indolyl, azaindolyl and substituted azaindolyl are each and individually attached to the maleimide moiety via a 3'-position of the indolyl and azaindolyl, respectively.

In an embodiment of the compound of the invention the indolyl and azaindolyl moiety, respectively, is multi-substituted and bearing 2-methyl, 5-methoxy, 5-halogen groups and the like.

A compound of the invention may exist in free or in salt form and/or solvate form or of the salt thereof. A "pharmaceutically acceptable salt" of a compound relates to a salt that is pharmaceutically acceptable and that possesses the desired pharmacological activity of the parent compound. "Physiologically or pharmaceutically acceptable salts" of a compounds of the invention include but are not limited to acid addition salts with a) inorganic acids, such as, for example, hydrochloric acid, hydrobromic acid, sulfuric acid, nitric acid or phosphoric acid and the like, or formed with b) organic acids, including but not limited to carboxylic acids, such as, e.g., acetic acid, tartaric acid, lactic acid, citric acid, maleic acid, malonic acid, succinic acid, ascorbic acid, fumaric acid, cinnamic acid, mandelic acid, benzoic acid, gluconic acid and the like, or c) sulfonic acids, such as, e.g., methane sulfonic acid, benzene sulfonic acid, toluene sulfonic acid, camphorsulfonic acid and the like.

Physiologically acceptable solvates are preferably hydrates.

Unless otherwise stated, the following terms used in the specification and claims have, in a preferred embodiment, the meanings given below:

The terms "alkyl" and "alkyloxy" as preferably used herein or in combination with other terms means linear or branched hydrocarbon structures and combinations thereof with one, two, three, four, five or six carbon atoms, including but not limited to, e.g., methyl, ethyl, propyol (iso-, n-), butyl (iso-, n-, tert-), pentyl, hexyl, methoxy, ethoxy, propoxy (iso-, n-), butoxy (iso-, n-, tert-), pentoxy, hexoxy and the like.

As preferably used herein the term "cycloalkyl" means mono- or polycyclic saturated or unsaturated three, four, five, six or seven ring carbocyclic alkyl groups, including but not limited to cyclopropyl, cyclobutyl, cyclopentyl, cyclohexyl, cycloheptyl, cyclobutenyl, cyclopentenyl, cyclopentadienyl, cyclohexyl, cyclohexenyl, cyclohexadienyl, cycloheptenyl, cycloheptadienyl and cycloheptatrienyl and the like.

The term "aryl" as preferably used herein means mono- and polycyclic aromatic groups having 6, 7, 8, 9, 10, 11, 12, 13 or 14 backbone carbon atoms, optionally fused to a carbocyclic group, including but not limited to phenyl, naphthyl, indenyl, indanyl, azulenyl, fluorenyl, 1,2,3,4-tetrahydronaphthyl, phenanthrenyl and the like.

The term "monoalkylamino" or "monoarylamino" as preferably used herein means a radical —NHR where R is an alkyl, cycloalkyl or aryl as defined herein, including but not limited to, e.g., methylamino, cyclohexylamino, phenylamino and the like.

The term "dialkylamino" or "diarylamino" as preferably used herein means a radical —NRR', where each of R and R' individually and independently represents an alkyl, cycloalkyl or aryl as defined herein, including but not limited to, e.g., dimethylamino, dicyclohexylamino, methylethylamino, diphenylamino and the like.

The term "alkylthio" or "arylthio" as preferably used herein means a radical —SR where R is an alkyl or aryl as defined herein, including but not limited to, e.g., methylthio, ethylthio, propylthio, butylthio, phenylthio and the like.

The term "acylamino" as preferably used herein means a radical -NR'C(O)R, where R' is hydrogen or alkyl, and R is hydrogen, alkyl, cycloalkyl, cycloalkylalkyl, phenyl or phenylalkyl, wherein alkyl, cycloalkyl, cycloalkylalkyl, and phenylalkyl are as defined herein. Representative examples include, but are not limited to, formylamino, acetylamino, cylcohexylcarbonylamino, benzoylamino and the like.

The term "haloalkyl" as preferably used herein means substituted alkyl as defined herein, wherein alkyl is substituted with one or more of same or different halogen atoms, including but not limited to, e.g., —CH$_2$Cl, —CF$_3$, —CH$_2$CF$_3$, —CH$_2$CCl$_3$ and the like.

The terms "alkylsufinyl" and "arylsulfinyl" as preferably used herein mean a —S(O)R group, where R is alkyl (in case of alkylsulfinyl) and aryl (in case of arylsulfinyl) as defined herein, including but not limited to, e.g., methylsulfinyl, ethylsulfinyl, propylsulfinyl, butylsulfinyl, each including all isomeric forms thereof, and the like.

The terms "alkylsulfonyl" and "arylsulfonyl" as preferably used herein mean a —S(O)$_2$R group, where R is alkyl (in case of alkylsulfonyl) and aryl (in case of arylsulfonyl) as defined herein, including but not limited to, e.g., methylsulfonyl, ethylsulfonyl, propylsulfonyl, butylsulfonyl, each including all isomeric forms thereof, and the like.

The terms "alkylsulfinamido" and arylsulfinamido" as preferably used herein mean a —S(O)NRR' group, where R and R' are hydrogen and/or alkyl (in case of alkylsulfinamido) and aryl (in case of arylsulfinamido) as defined herein, including but not limited to, e.g., tert-butanesulfinamide, p-toluenesulfinamide and the like.

The terms "alkylsulfonamido" and arylsulfonamido" as preferably used herein mean a —S(O)$_2$NRR' group, where R and R' are hydrogen and/or alkyl (in case of alkylsulfonamido) and aryl (in case of arylsulfonamido) as defined herein, including but not limited to, e.g., methansulfonamide and the like.

The term "heteroaryl" as preferably used herein means mono- or bi-carbocyclic aromatic groups with 1, 2, 3 or 4 ring-heteroatoms selected from N, S and O. Preferably, a total number of ring atoms is 5, 6, 7, 8, 9 or 10. Examples without limitation of heteroaryl groups are benzofuranyl, furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolynyl, purinyl, carbazolyl, benzoxazolyl, benzamidazolyl, indolyl, isoindolyl, diazinyl, pyrazinyl, triazinyl, tetrazinyl, tetrazolyl, benzothiophenyl, benzopyridyl, benzimidazolyl and derivatives thereof. The heteroaryl ring is optionally substituted independently with one or more substituents, wherein each and any substituent is individually and independently selected from alkyl, haloalkyl, heteroalkyl, alkoxy, hydroxy, halogen, nitro, cyano groups and the like, preferably as defined herein.

The term "heterocyclyl" as preferably used herein means a mono- or polycyclic saturated or unsaturated non-aromatic heterocyclyl groups of 5, 6, 7 or 8 ring atoms in which one or two ring atoms are heteroatoms selected from NR (where R is independently hydrogen or alkyl, preferably as defined herein), O, or $S(O)_n$ (where n is an integer from 0, 1 and 2), the remaining ring atoms being carbon atoms, where one or two carbon atoms may optionally be replaced by a carbonyl group. The heterocyclyl ring may be optionally substituted independently with one, two or three substituents, wherein each substituent is individually and independently selected from alkyl, haloalkyl, heteroalkyl, halogen, nitro, cyano, hydroxy, alkoxy, amino, mono- or dialkylamino, acyl, preferably as defined herein. Examples for heterocyclyl groups include but are not limited to tetrahydrofuranyl, tetrahydropyranyl, imidazolinyl, imidazolidinyl, pyrrolidinyl, piperidinyl, piperazinyl, morpholinyl, thiomorpholinyl, N-methylpiperidin-3-yl, N-methylpyrrolidin-3-yl, pyrrolinyl and derivatives of each thereof.

The term "halogen" as preferably used herein means a halogen atom selected from fluorine, chlorine, bromine and iodine, preferably the halogen atom is either fluorine or chlorine, more preferably the halogen atom is fluorine.

The term "protected" as preferably used herein means those organic groups intended to protect nitrogen atoms against undesirable reactions during synthetic procedures. Suitable nitrogen protecting groups are well known in the art and include but are not limited to, e.g., trimethylsilyl, tert-butyldimethylsilyl (TBDMS), benzyl, benzyloxycarbonyl (Cbz), 9-fluorenylmethoxycarbonyl (Fmoc), tert-butoxycrbonyl (Boc), trifluoroacetyl, 2-trimethylsilylethanesulfonyl (SES), and the like. Other suitable nitrogen protecting groups which are suitable for the practicing of the invention can be found in the publication of T. W. Greene and G. M. Wuts, "Protecting Groups in Organic Synthesis", Second Edition, Wiley, New York, 1991, and references cited therein.

Numerous additional aspects and advantages of the invention will become apparent to those skilled in the art upon consideration of the following detailed description of the invention which describes presently preferred embodiments thereof.

The invention also relates to the metabolites and prodrugs of the compound of the invention. Preferably, a prodrug of a compound of the invention is prepared by modifying functional groups present in the compound of the invention in such a way that the modifications may be cleaved in vivo to release a or the active compound. Preferably, such active compound is a compound of the invention or a compound derived therefrom having at least one characteristic of a compound of the invention. Preferably, such characteristic is the capacity to inhibit GSK3β and/or is suitability for the treatment of leukemia.

In accordance therewith the term "prodrug" refers to (a) an inactive form of a drug that exerts its effects after metabolic processes in vivo, when such prodrug is administered to a mammalian subject, to release an active parent drug and preferably a compound of the invention, or (b) a substance that gives rise to a pharmacologically active metabolite, although not itself active (i.e. an inactive precursor). Examples of prodrugs include, but are not limited to esters, carbamates and the like.

As preferably used herein the term "metabolite" refers to a) a product of metabolism, including an intermediate and an end product, b) any substance in metabolism (either as product of metabolism or as necessary for metabolism), or c) any substance produced or used during metabolism. More preferably, the term "metabolite" refers to an end product that remains after metabolism.

As preferably used herein, the term "pharmaceutically acceptable excipient" an excipient that is useful in preparing a pharmaceutical composition that is generally safe, non-toxic and neither biologically nor otherwise undesirable, or adversely affects the therapeutic benefit of the compound of the invention. A "pharmaceutically acceptable excipient" as preferably used in the specification and claims includes both one and more than one such excipient. Such excipient may be any solid, liquid, semi-solid. Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, and the like.

As preferably used herein, the term "therapeutically effective amount" means the amount of a compound of the invention formula (I) that, when administered to a mammal for treating a disease, is sufficient to effect such treatment for the disease. The "therapeutically effective amount" will vary depending on the compound, the disease and its severity and the age, weight, etc., of the mammal to be treated.

As preferably used herein, "treating" or "treatment" of a disease includes: (1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

As preferably used herein, the term "leukemia" means a disease characterized by an abnormal proliferation (production by multiplication) of blood cells, usually white blood cells (leukocytes). Leukemia as preferably used herein includes acute and chronic forms. Acute leukemia is characterized by the rapid proliferation of immature blood cells. This crowding makes the bone marrow unable to produce healthy blood cells.

As preferably used herein, the term "treatment of leukemia" includes partial or total inhibition of leukemia in a subject, as well as partial or total destruction of the leukemic cells.

As preferably used herein, the term "prevention of leukemia" includes preventing the onset of clinically evident leukemia as well as preventing the onset of a preclinical evident stage of leukemia in subjects at risk.

In a preferred embodiment of the invention, leukemia is resistant leukemia and in particular multidrug resistant leukemia, i.e., the leukemic cells exhibit resistance to conventional chemotherapeutics, preferably the MDR (multidrug resistance) phenotype.

In an embodiment, the compound of the invention is a compound, a physiologically acceptable salt thereof or a physiologically acceptable solvate thereof, which is capable of stimulating apoptosis in leukemic cells.

The present invention thus also relates to the use of a compound of the invention, a physiologically acceptable salt or solvate thereof, preferably as defined herein, in combination with one or more than one further chemotherapeutic agent.

In an embodiment of the invention, the treatment of the subject comprises further stimulation of cell death by a conventional method or combination of conventional methods. The conventional methods preferably being selected from the group consisting of irradiation, e.g. external irradiation or administration of radioactive compounds, bone marrow transplantation and treatment with a chemotherapeutic agent which is including antineoplastic agents, multidrug resistance reversing agents, and biological response modifiers, and combinations thereof.

The present invention thus also relates to the use of a compound of the invention, a physiologically acceptable salt or a solvate thereof, preferably as defined herein, in combination with one or more than one further chemotherapeutic agent. Suitable antineoplastic agents may be selected from the group comprising asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, lomustine, mechlorethamine, melphalan, mercaptopurine, methotrexate, mitomycin, mitoxantrone, pentostatin, procarbazine, 6-thioguanine, topotecan, vinblastine, vincristine, dexamethasone, retinoic acid and prednisone. Preferred examples for antineoplastic agents to be used in the treatment of leukemia in accordance with the present invention, especially in the treatment of AML which his acute myeloid leukemia, or ALL which is acute lymphoblastic leukemia, comprise cytarabine, etoposide, mitoxantron, cyclophosphamide, retinoic acid, daunorubicin, doxorubicin and idarubicin.

When a compound of the invention, a physiologically acceptable salt or a solvate thereof is used as an active ingredient in the uses, methods and compositions of the present invention, it can be incorporated into standard pharmaceutical dosage forms, which the skilled artisan is familiar with. Basically, any pharmaceutical dosage form may be used in the invention.

The present invention thus also relates to a pharmaceutical composition comprising a pharmaceutically acceptable auxiliary agent in addition to a compound of the invention, a physiologically acceptable salt or solvate thereof as defined above. Such auxiliary agents are known in the art. e.g., the usual pharmaceutical excipients, diluents and adjuvants, e.g., organic and inorganic inert carrier materials such as water, gelatine, lactose, starch, magnesium stearate, talc, vegetable oils, gums, polyalkylene glycols, etc. These pharmaceutical preparations can be employed in a solid form, e.g., as tablets, capsules, or they can be administered in liquid form, e.g., as solutions, suspensions or emulsions.

Further pharmaceutical excipients and adjuvants which may be added to a pharmaceutical composition of the invention, include preservatives, antioxidants, antimicrobial agents and other stabilizers; wetting, emulsifying and suspending agents, and anti-caking compounds; fragrance and coloring additives; compositions for improving compressibility, or agents to create a delayed, sustained or controlled release of the active ingredient; and various salts to change the osmotic pressure of the pharmaceutical preparation or to act as buffers. Such excipients and adjuvants are known to the skilled artisan.

It will be acknowledged by a person skilled in the art that a or the compound of the invention is any compound disclosed herein, including but not limited to any compound described in any of the above embodiments and any of the following embodiments.

It will be acknowledged by a person skilled in the art that a or the method of the invention is any method disclosed herein, including but not limited to any method described in any of the above embodiments and any of the following embodiments.

It will be acknowledged by a person skilled in the art that a or the composition of the invention is any composition disclosed herein, including but not limited to any composition described in any of the above embodiments and any of the following embodiments.

As to the synthesis of the compound of the invention a person skilled in the art will acknowledge the following. Disubstituted maleimide and particularly bisindolylmaleimide subunit is present in a number of biologically active compounds. Among these arcyriarubins (Scheme 1; a) represent the simplest members of the naturally occurring 3,4-bisindolylmaleimides. They are structurally related to the arcyriaflavines (b) and to the aglycon of well-known staurosporine (c), rebeccamycine (d) and other biologically active metabolites.

Scheme 1. Arcyriarubins (a), arcyriaflavins (b), staurosporine (c), and rebeccamycine (d).

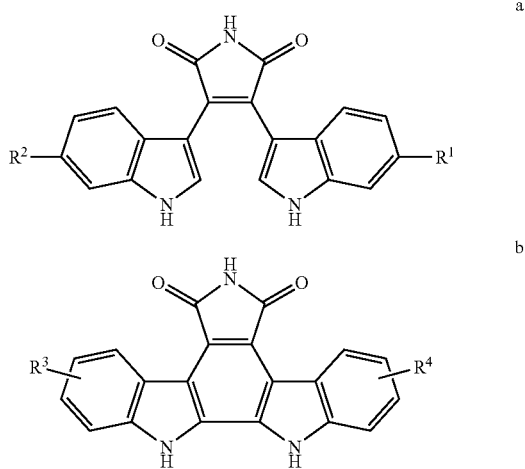

-continued

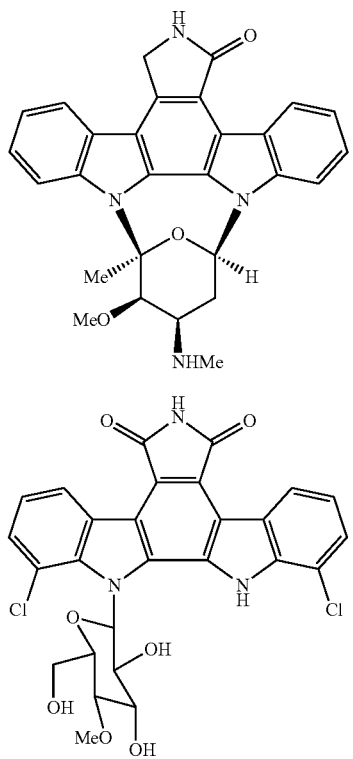

Interestingly, synthetic analogues possess wide spectra of antibacterial, antiviral, antimicrobial and antigenic activities. Furthermore, derivatives of this class of compounds are promising agents for autoimmune diseases, like diabetes and cancer, as well as valuable inhibitors of different protein kinases, especially PKC, which plays an important role in many signal transduction pathways, or GSK3β, therefore, may be used for the treatment of GSK3β mediated diseases. Notably, some derivatives are currently evaluated in human clinical trails as anticancer drugs. For example, Enzastaurin, which is developed by Eli Lilly and Company, is a synthetic bisindolylmaleimide derivative with potential antineoplastic activity and can be used for the treatment of solid tumors (WO02/02094, WO02/02116, and IL165747). In January 2009 Enzastaurin was in the phase III of the clinical trials. This agent may decrease tumor blood supply, preventing its growth. Ruboxistaurin, another bisindolylmaleimid, is an investigational drug for diabetic peripheral retinopathy, was also developed by Eli Lilly, and is presently in a phase III study. Ruboxistaurin is an inhibitor of PKC-beta. Other examples of indolylmaleimide agents have been described in WO2009/071620 and WO 2006/061212. Namely, certain 3-(indolyl)- or 3-(azaindolyl)-4-arylmaleimide derivatives act as angiogenesis inhibitors therefore were proposed their use for controlling angiogenesis and/or vascular dysfunction as well as for treatment of leukemia.

Obviously, it is very important to develop new strategies to the new derivatives of this class of bioactive compounds that would show more improved properties, such as enhanced bioavailability, increased metabolic stability, and improved selectivities toward action targets that they can be used as targeted drugs.

As a result of pharmaceutical importance of 3,4-bisindolylmaleimides, a variety of approaches have been reported in the literature for their synthesis. The most widely used methods were developed by groups of W. Steglich (Tetrahedron, 1988, 44, 2887) and M. Faul (JOC, 1998, 63, 6053). Both methods allow the synthesis of symmetrically and unsymmetrically di-substituted maleimides. According to the Steglich procedure indolyl magnesium bromide reacts with 3,4-dibromomaleimide to give mono- or di-substituted products. The outcome of this reaction is strongly dependent on the solvent. The procedure of Faul et al. involves a one step condensation of substituted (aryl or indolyl) acetamides with substituted (aryl or indolyl) glyoxyl esters in the presence of strong base.

Several indolylmaleimide compounds can be also prepared according to the known methods, which are disclosed, for example in WO02/38561, EP328026, WO03/095452 and WO2006/061212.

Selected compounds of this invention were prepared according to the reference "Org. Biomol. Chem. 2008, 6, 992". Typically in a two step sequence first was synthesized 3-halo-4-indolyl- or azaindolylmaleimide derivative, starting from commercially available indole or azaindole derivative and 3,4-dihalomaleimide. In particular case 2-methylindole (1) reacted with 3,4-dibromomaleimide (2) to form 3-bromo-1-methyl-4-(2-methyl-3-indolyl)-maleimide (3) (Scheme 2).

Scheme 2

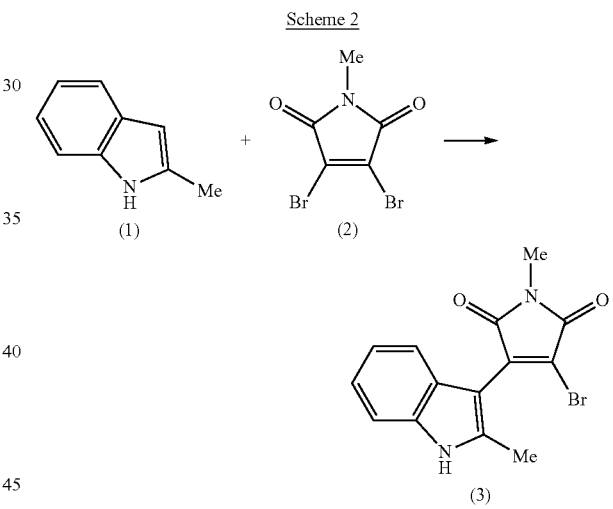

Using Grignard reagent according to the protocol of Steglich led to the desired mono-substituted product in 68% isolated yield. In addition, a minor amount of the corresponding di-substituted product (5%) was isolated. However, applying the modification of Ohkubo (Tetrahedron, 1996, 52, 8099), which means metallation of indole with lithium hexamethyldisilazane (LiHMDS) and further reaction with one equivalent of dibromo compound 2, led to 3-bromo-1-methyl-4-(2-methyl-3-indolyl)-maleimide (3) in excellent selectivity and nearly quantitative yield (98%).

Aryl, heteroaryl or heterocyclyl substituents were introduced in the 4-position of maleimide moiety using Suzuki coupling reaction of compound 3 with various substituted or non substituted aryl, heteroaryl or heterocyclyl boronic acids. The coupling reactions were preferably performed in the presence of 0.05 to 4 mol % Pd(OAc)$_2$ and suitable phosphine ligand. Depend on steric and electronic factors good to excellent yield of the corresponding product of formula (I) was obtained. For example, Suzuki coupling reaction of 3-bromo-1-methyl-4-(2-methyl-3-indolyl)-maleimide (3) with phenylboronic acid (4) led to 1-methyl-3-(2-methyl-1H-indol-3-yl)-4-phenyl-1H-pyrrole-2,5-dione (5) in quantitative yield (Scheme 3).

Scheme 3

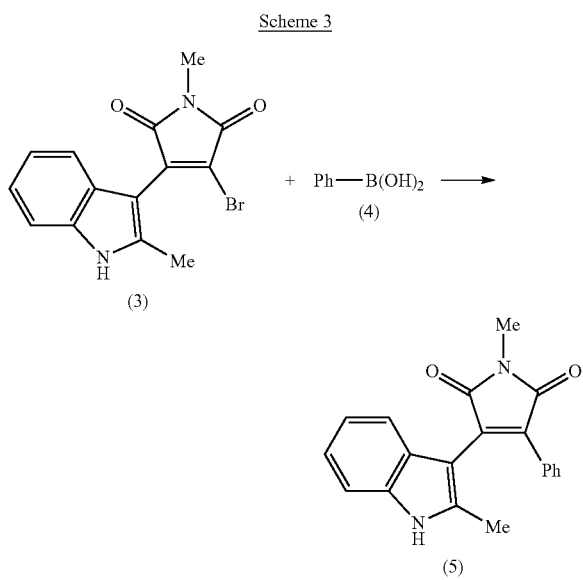

All coupling products are bright colored, stabile crystalline compounds. The resulting 3-indolyl-4-aryl(heteroaryl or heterocyclyl) maleimides constitute new biologically active compounds. Protection and deprotection steps of indole nitrogen are not necessary.

As will be apparent to a person skilled in the art, compound of formula (I) wherein X is N—R¹, can be converted to other compound of formula (III) (Scheme 4).

Scheme 4

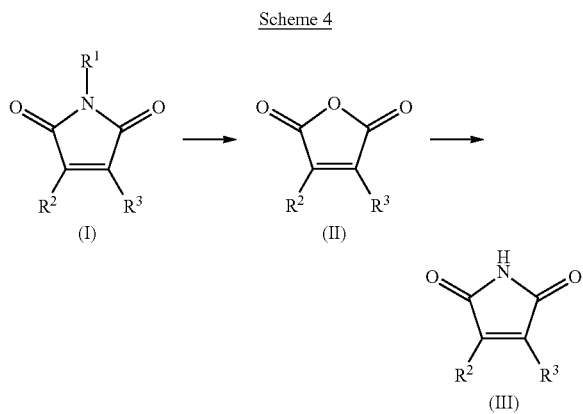

For example, treatment of at maleimide moiety protected compound of formula (I) with strong base, such as sodium or potassium hydroxide led to the formation of corresponding cyclic anhydrides of formula (II), which are easily converted to unprotected compounds of formula (III) over heating with ammonium acetate.

Both conversions proceed in high to excellent yields. Also these products are bright colored, stabile crystalline compounds.

The certain compounds of present invention, during the biological tests as GSK3β inhibitors, unexpectedly have shown cyctotoxic properties and are able to induce apoptosis in leukemic cells.

The present invention is now further illustrated by reference to the following figures and examples from which further advantages, features, and embodiments may be taken, wherein FIG. 1 is a diagram showing the inhibition of GSK3β by compound PDA-66 at different concentrations;

EXAMPLES

Figure 1:
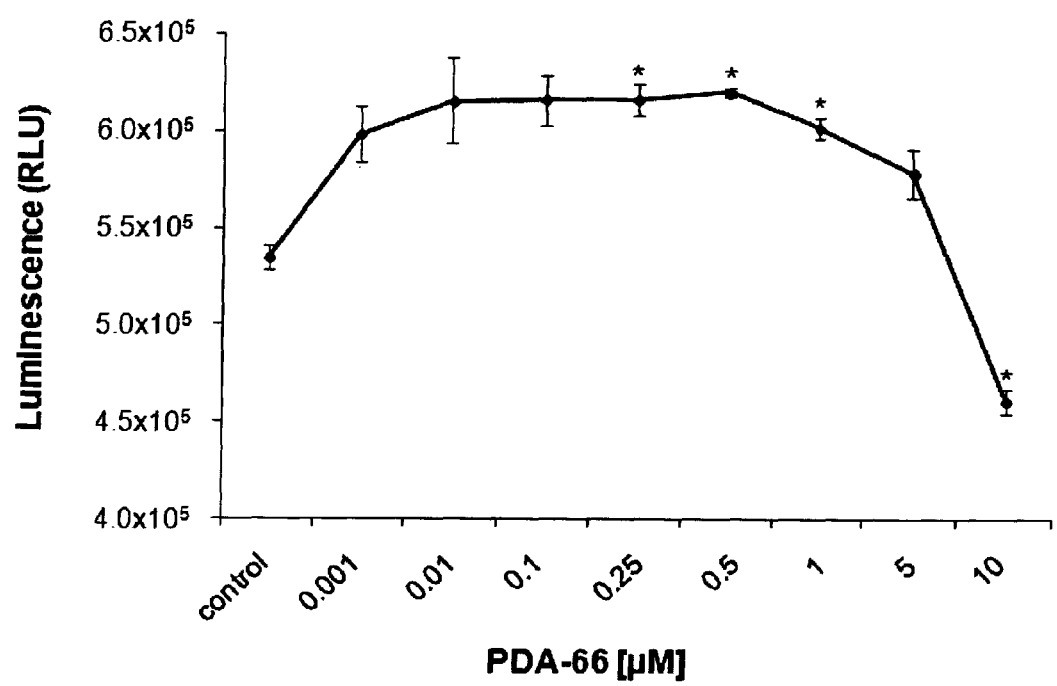

Abbreviations used in general procedures and examples are defined as follows: "HCl" for hydrochloric acid, "KOH" for potassium hydroxide, "NaHC0₃" for sodium hydrocarbonate, "K₂CO₃" for potassium carbonate, "Na₂SO₄" for sodium sulfate, "CH₂Cl₂" for methylene chloride, "THF" for tetrahydrofuran, "EA" for ethyl acetate, "DMSO" for dimethylsulfoxide, "CDCl₃" for deuterated chloroform, "TLC" for thin layer chromatography, "LiHMDS" for lithium hexamethyldisilazane, "Pd(OAc)₂" for palladium acetate.

All reactions were carried out under argon atmosphere. Reactions were monitored by TLC analysis (pre-coated silica gel plates with fluorescent indicator UV254, 0.2 mm) and visualized with 254 nm UV light or iodine. Chemicals were purchased from Aldrich, Fluka, Acros, AlfaAsar, Strem and unless otherwise noted were used without further purification. All compounds were characterized by ¹H NMR, ¹³C NMR, GC-MS, HRMS and IR spectroscopy. ¹H spectra were recorded on Bruker AV 300 and AV 400 spectrometers. ¹³C NMR and ¹⁹F NMR spectra were recorded at 75.5 MHz and 282 MHz respectively. Chemical shifts are reported in ppm relative to the center of solvent resonance. Melting points were determined on a digital SMP3 (Stuart). IR spectra were recorded on FT-IR ALPHA (Bruker) with Platinum-ATR (Bruker). EI (70 eV) mass spectra were recorded on MAT 95XP (Thermo ELECTRON CORPORATION). GC was performed on Agilent 6890 chromatograph with a 30 m HP5 column. HRMS was performed on MAT 95XP (EI) and Agilent 6210 Time-of-Flight LC/MS (ESI).

GC-MS was performed on Agilent 5973 chromatograph Mass Selective Detector. All yields reported refer to isolated yields.

Example 1: Preparation 1—General Procedure for Condensation of Indole or Azaindoles Derivative with 3,4-dihalomaleimide Compound and Specific Compounds The (aza)indole derivative (10 mmol) was dissolved in dry THF (20 ml) and cooled under Argon to −20° C., before 21 ml of LiHMDS (1 M in THF) were slowly added. After stirring for 2 h at −20° C., a solution of 3,4-dihalomaleimide derivative (10 mmol) in THF (20 ml) was added to the lithiated (aza)indole solution all at once via syringe. After stirring additional 1 h at −20° C. (TLC control), the reaction mixture was carefully neutralized with 2N aq HCl and extracted with ethyl acetate (3×). The combined organics were washed with sat. aq $NaHCO_3$, brine, and water. After drying over $Na_2SO_4$ and concentration, the crude material was crystallized from ether.

Example 1.1

3-Bromo-1-methyl-4-(2-methyl-1H-indol-3-yl)-1H-pyrrole-2,5-dione

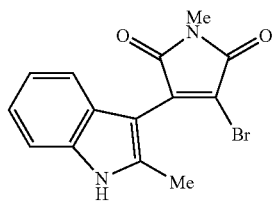 [SMILES: Cc1[nH]c2ccccc2c1C1=C(Br)C(=O)N(C)C1=O]

Orange crystals; $^1$H NMR (CDCl$_3$) δ 2.48 (s, 3H), 3.19 (s, 3H), 7.18 (ddd, 1H), 7.20 (ddd, 1H), 7.31 (ddd, 1H), 7.48 (m, 1H), 8.48 (br.s, 1H); $^{13}$C NMR (CDCl$_3$) δ 14.3, 24.9, 102.0, 110.8, 120.5, 120.7, 120.8, 122.4, 126.4, 135.5, 137.6, 139.3, 166.4, 169.1; GC-MS (EI, 70 eV): m/z (%) 318 (100) [M$^+$], 320 (96) [M$^+$]; HRMS (EI): Cacld for $C_{14}H_{11}O_2N_2Br$: 317.99984; found: 317.99979; IR (ATR, cm$^{-1}$): 3361, 3066, 1771, 1703, 1623, 1422, 1379, 990, 806, 749, 733, 656.

Example 1.2

3-Bromo-1-methyl-4-(1H-pyrrolo[2,3-b]pyridin-3-yl)-1H-pyrrole-2,5-dione

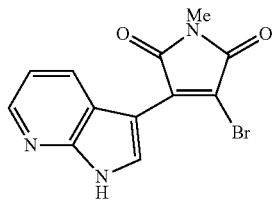 [SMILES: CN1C(=O)C(Br)=C(c2c[nH]c3ncccc23)C1=O]

Preparation was performed using Grignard reagent. Orange crystals; $^1$H NMR (DMSO-d$_6$) δ 2.99 (s, 3H), 7.21 (ddd, 1H, J~3.83, 5.31, 7.36 Hz), 8.20 (s, 1H), 8.31 (dd, 1H, J=1.53, 3.52 Hz), 8.33 (s, 1H), 12.68 (br.s, 1H); $^{13}$C NMR (DMSO-d$_6$) δ 24.6, 102.7, 114.8, 116.9, 117.0, 130.8, 131.2, 136.8, 144.0, 148.7, 166.4, 168.9; GC-MS (EI, 70 eV): m/z (%) 305 (58) [M$^+$], 307 (57) [M$^+$]; HRMS pos. (ESI): Calc for [M+H]$^+$, $C_{12}H_9BrN_3O_2$: 305.98727 and 307.98532; found: 305.98737 and 307.98544; IR (ATR, cm$^{-1}$): 3079, 2742, 1764, 1707, 1584, 1488, 1440, 1419, 1384, 1287, 1167, 1141, 1101, 801, 778, 733, 628.

Example 1.3

1-Methyl-3,4-bis-(2-methyl-1H-indol-3-yl)-1H-pyrrole-2,5-dione

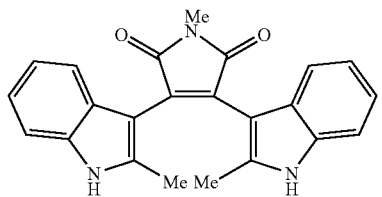 [SMILES: Cc1[nH]c2ccccc2c1C1=C(c2c(C)[nH]c3ccccc23)C(=O)N(C)C1=O]

Red crystals; $^1$H NMR (DMSO-d$_6$) δ 1.97 (s, 3H), 1.98 (s, 3H), 3.05 (s, 3H), 6.75 (br.t, 2H, J=7.41 Hz), 6.95 (ddd, 2H, J~3.83, 5.31, 7.36 Hz), 7.03 (br.d, 2H, J=7.90 Hz), 7.23 (br.d, 2H, J=8.09 Hz), 11.29 (br.s, 2H); $^{13}$C NMR (DMSO-d$_6$) δ 13.0, 23.9, 103.3, 110.7, 119.2, 119.4, 120.8, 126.6, 131.2, 135.5 (2C), 137.3, 170.4, 171.3; GC-MS (EI, 70 eV): m/z (%) 369 (100) [M$^+$]; HRMS (EI): Cacld for $C_{23}H_{19}O_2N_3$: 369.14718; found 369.14705; IR (ATR, cm$^{-1}$): 3383, 3307, 1755, 1692, 1456, 1435, 1377, 1239, 1049, 1022, 1003, 747, 737, 693.

Example 2: Preparation 2—General Procedure for Suzuki Coupling and Specific Compounds In an Ace-pressure tube into a solution of (aza)indolyl-maleimide derivative (1 mmol) and corresponding boronic acid (1.5 mmol) in dimethoxyethane (3 ml) were added $K_2CO_3$ (1M in water, 3 ml), Pd(OAc)$_2$ (2 mol %) and ligand (2.5 mol %) under argon atmosphere. The pressure tube was fitted with a Teflon cap and heated at 100° C. (TLC control). The mixture was cooled to room temperature and diluted with ethyl acetate. The organic layer was washed with sat. aq ammonium chloride (2×30 mL) and water. After drying over $Na_2SO_4$ and removal of the solvent in vacuum, the coupling product was isolated by column chromatography in heptane/ethyl acetate.

Example 2.4

1-Methyl-3-(2-methyl-1H-indol-3-yl)-4-(4-vinylphenyl)-1H-pyrrole-2,5-dione

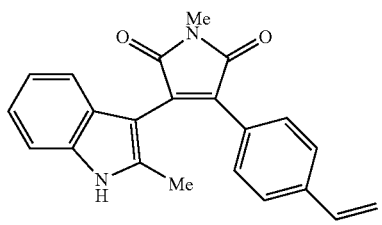 [SMILES: C=Cc1ccc(C2=C(c3c(C)[nH]c4ccccc34)C(=O)N(C)C2=O)cc1]

Red-orange crystals; $^1$H NMR (CDCl$_3$) δ 2.14 (s, 3H), 3.17 (s, 3H), 5.25 (dd, 1H, J=0.66, 10.89 Hz), 5.72 (dd, 1H, J=0.70, 17.61 Hz), 6.63 (dd, 1H, J=10.88, 17.62 Hz), 6.96 (m, 1H), 7.09 (m, 2H), 7.23 (m, 1H), 7.27 (m, 2H), 7.53 (m, 2H), 8.32 (br s, 1H); $^{13}$C NMR (CDCl$_3$) δ 13.7, 24.2, 103.0, 110.5, 115.0, 120.3, 120.5, 122.0, 126.1 (2C), 126.5, 129.5 (2C), 129.6, 132.7, 133.7, 135.7, 136.2, 136.8, 138.1, 171.2, 171.6; GC-MS (EI, 70 eV): m/z (%) 342 (100) [M$^+$]; HRMS (EI): Cacld for C$_{22}$H$_{18}$O$_2$N$_2$: 342.13628; found: 342.13618; IR (ATR, cm$^{-1}$): 3380, 3053, 2920, 1745, 1689, 1456, 1428, 1383, 1235, 990, 903, 847, 814, 741, 656.

Example 2.5

1-Methyl-3-(2-methyl-1H-indol-3-yl)-4-phenyl-1H-pyrrole-2,5-dione

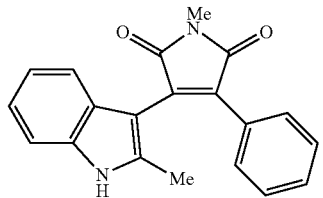 [SMILES: Cc1[nH]c2ccccc2c1C1=C(c2ccccc2)C(=O)N(C)C1=O]

Red crystals; $^1$H NMR (CDCl$_3$) δ 2.14 (s, 3H), 3.20 (s, 3H), 6.97 (ddd, 1H), 7.11 (m, 2H), 7.22 (ddd, 1H), 7.27 (m, 3H), 7.55 (m, 2H), 8.33 (br.s, 1H); $^{13}$C NMR (CDCl$_3$) δ 13.6, 24.2, 102.8, 110.5, 120.3, 120.5, 122.0, 126.5, 128.4 (2C), 129.1, 129.3 (2C), 130.2, 133.2, 134.1, 135.7, 136.8, 171.2, 171.5; GC-MS (EI, 70 eV): m/z (%) 316 (100) [M$^+$]; HRMS (EI): Cacld for C$_{20}$H$_{16}$O$_2$N$_2$ 316.12063; found: 316.12091; IR (ATR, cm$^{-1}$): 3426, 3381, 3052, 1759, 1690, 1618, 1435, 1422, 1382, 1234, 1002, 989, 938, 786, 752, 736, 693.

Example 2.6

3-(4-Acetylphenyl)-1-methyl-4-(2-methyl-1H-indol-3-yl)-1H-pyrrole-2,5-dione (PDA-66)

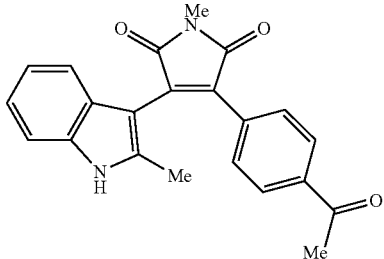 [SMILES: CC(=O)c1ccc(C2=C(c3c(C)[nH]c4ccccc34)C(=O)N(C)C2=O)cc1]

Red crystals; $^1$H NMR (CDCl$_3$) δ 2.18 (s, 3H), 2.57 (s, 3H), 3.21 (s, 3H), 6.94 (ddd, 1H, J~0.99, 7.05, 8.00 Hz), 7.03 (ddd, 1H), 7.11 (ddd, 1H, J 1.15, 7.05, 8.11 Hz), 7.25 (dd, 1H, J~0.41, 8.11 Hz), 7.67 (ddd, 2H, J~1.72, 3.63, 8.61 Hz), 7.84 (ddd, 2H, J~1.85, 3.70, 8.61 Hz), 8.57 (br.s, 1H); $^{13}$C NMR (CDCl$_3$) δ 13.8, 24.3, 26.6, 102.5, 110.7, 120.1, 120.6, 122.2, 126.2, 128.2 (2C), 129.5 (2C), 131.9, 134.9, 135.0, 135.8, 136.6, 137.6, 170.8, 171.1, 197.8; GC-MS (EI, 70 eV): m/z (%) 358 (100) [M$^+$]; HRMS (EI): Cacld for C$_{22}$H$_{18}$O$_3$N$_2$: 358.13119; found: 358.131088; IR (ATR, cm$^{-1}$): 3339, 3058, 2923, 1762, 1692, 1678, 1427, 1407, 1383, 1358, 1265, 1234, 990, 846, 817, 742.

Example 2.7

3-(2,6-Dimethylphenyl)-1-methyl-4-(2-methyl-1H-indol-3-yl)-1H-pyrrole-2,5-dione

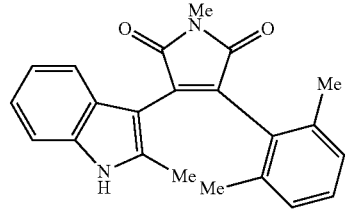 [SMILES: Cc1cccc(C)c1C1=C(c2c(C)[nH]c3ccccc23)C(=O)N(C)C1=O]

Orange crystals; $^1$H NMR (CDCl$_3$) δ 1.97 (d, 3H, J=0.88), 2.08 (s, 6H), 3.22 (s, 3H), 7.00 (ddd, 1H), 7.01 (d, 2H), 7.10 (ddd, 1H), 7.12 (ddd, 1H), 7.19 (ddd, 1H), 7.25 (ddd, 1H), 8.21 (br.s, 1H); $^{13}$C NMR (CDCl$_3$) δ 13.2, 20.7 (2C), 24.4, 103.6, 110.3, 119.9, 120.6, 122.1, 126.8, 128.0 (2C), 128.8, 129.5, 135.4, 136.1, 136.9, 137.0 (2C), 137.1, 171.0, 171.2; GC-MS (EI, 70 eV): m/z (%) 344 (100) [M$^+$]; HRMS (ED: Cacld for C$_{22}$H$_{20}$O$_2$N$_2$: 344.15193; found: 344.15175; IR (ATR, cm$^{-1}$): 3342, 2951, 1763, 1689, 1433, 1381, 1229, 987, 739, 665.

Example 2.8

3-(3-Chlorophenyl)-1-methyl-4-(2-methyl-1H-indol-3-yl)-1H-pyrrole-2,5-dione

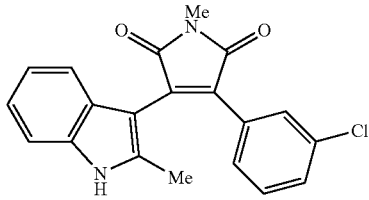 [SMILES: Cc1[nH]c2ccccc2c1C1=C(c2cccc(Cl)c2)C(=O)N(C)C1=O]

Red crystals; $^1$H NMR (CDCl$_3$) δ 2.20 (s, 3H), 3.20 (s, 3H), 6.98 (ddd, 1H, J~1.03, 7.0, 8.03 Hz), 7.05 (br.d, 1H, J~7.52 Hz), 7.13 (ddd, 1H, J~1.23, 7.0, 8.14 Hz), 7.18 (br.t, 1H, J=7.91 Hz), 7.25 (m, 2H), 7.40 (ddd, 1H, J~1.26, 2.72, 7.84 Hz), 7.62 (br.t, 1H, J=1.80 Hz), 8.36 (br.s, 1H); $^{13}$C NMR (CDCl$_3$) δ 13.8, 24.3, 102.6, 110.6, 120.3, 120.7, 122.2, 126.2, 127.5, 129.1, 129.2, 129.6, 131.9, 132.1, 134.2, 134.3, 135.85, 137.2, 170.8, 171.1; GC-MS (EI, 70 eV): m/z (%) 350 (100) [M$^+$]; HRMS (EI): Cacld for C$_{20}$H$_{15}$O$_2$N$_2$Cl: 350.08166; found: 350.08115; IR (ATR, cm$^{-1}$): 3350, 3068, 2909, 1764, 1689, 1433, 1383, 1235, 991, 743, 735, 715, 683.

Example 2.9

3-(2,4-Dichlorophenyl)-1-methyl-4-(2-methyl-1H-indol-3-yl)-1H-pyrrole-2,5-dione

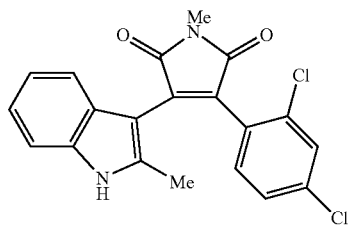 [SMILES: Cc1[nH]c2ccccc2c1C1=C(c2ccc(Cl)cc2Cl)C(=O)N(C)C1=O]

Orange crystals; $^1$H NMR (CDCl$_3$) δ 2.11 (s, 3H), 3.21 (s, 3H), 6.99 (ddd, 1H, J~1.03, 7.0, 8.03 Hz), 7.10 (ddd, 1H, J~0.93, 7.09, 8.23 Hz), 7.18 (m, 2H), 7.19 (d, 2H, J~1.20 Hz), 7.40 (br.t, 1H, J=1.15 Hz), 8.41 (br.s, 1H); $^{13}$C NMR (CDCl$_3$) δ 13.5, 24.4, 103.1, 110.6, 119.7, 120.8, 122.2, 126.7, 127.3, 128.5, 130.1, 132.1, 132.4, 134.7, 135.5, 137.5, 137.6, 170.1, 170.6; GC-MS (EI, 70 eV): m/z (%) 384 (100) [M$^+$]; HRMS (EI): Cacld for C$_{20}$H$_{14}$O$_2$N$_2$Cl$_2$: 384.04268; found: 384.04261; IR (ATR, cm$^{-1}$): 3358, 3064, 2949, 1756, 1687, 1436, 1386, 1228, 992, 857, 810, 778, 741, 673, 666.

Example 2.10

1-Methyl-3-(2-methyl-1H-indol-3-yl)-4-(thiophen-3-yl)-1H-pyrrole-2,5-dione

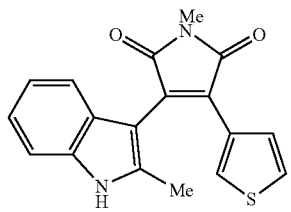 [SMILES: Cc1[nH]c2ccccc2c1C1=C(c2ccsc2)C(=O)N(C)C1=O]

Red crystals; $^1$H NMR (CDCl$_3$) δ 2.27 (s, 3H), 3.18 (s, 3H), 7.01 (ddd, 1H, J~1.07, 7.07, 8.05 Hz), 7.12 (ddd, 1H), 7.137 (dd, 1H, J~3.02, 5.15 Hz), 7.14 (ddd, 1H), 7.19 (dd, 1H, J=1.22, 5.17 Hz), 7.25 (dt, 1H, J=0.91, 8.06 Hz), 8.11 (dd, 1H, J=1.24, 2.95 Hz), 8.42 (br.s, 1H); $^{13}$C NMR (CDCl$_3$) δ 13.5, 24.2, 102.9, 110.6, 120.1, 120.5, 122.0, 125.1, 126.7, 127.5, 129.2, 130.0, 130.2, 130.5, 135.7, 136.7, 171.5, 171.6; GC-MS (EI, 70 eV): m/z (%) 322 (100) [M$^+$]; HRMS (EI): Cacld for C$_{18}$H$_{14}$O$_2$N$_2$S: 322.07705; found: 322.07631; IR (ATR, cm$^{-1}$): 3391, 3102, 1756, 1689, 1624, 1438, 1410, 1382, 1334, 1228, 1071, 1003, 989, 820, 804, 790, 752, 737, 653.

Example 2.11

1-Methyl-3-(2-methyl-1H-indol-3-yl)-4-(pyridin-4-yl)-1H-pyrrole-2,5-dione

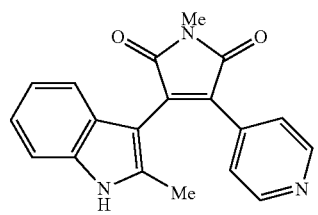 [SMILES: Cc1[nH]c2ccccc2c1C1=C(c2ccncc2)C(=O)N(C)C1=O]

Red crystals; $^1$H NMR (CDCl$_3$) δ 2.28 (s, 3H), 3.21 (s, 3H), 6.97 (m, 2H), 7.14 (ddd, 1H, J~3.58, 4.69, 8.23 Hz), 7.30 (dt, 1H, J~0.7, 8.15 Hz), 7.46 (2dd, 2H, J~1.59, 4.57 Hz), 8.53 (2dd, 2H, J~1.57, 4.62 Hz), 8.71 (br.s, 1H); $^{13}$C NMR (CDCl$_3$) δ 14.1, 24.4, 102.5, 110.8, 120.3, 120.9, 122.5, 123.3 (2C), 125.9, 139.9, 135.9, 136.5, 137.9, 138.1, 149.8 (2C), 170.3, 170.6; GC-MS (EI, 70 eV): m/z (%) 317 (100) [M$^+$]; HRMS (EI): Cacld for C$_{19}$H$_{15}$O$_2$N$_3$: 317.11588; found: 317.11635; IR (ATR, cm$^{-1}$): 3342, 2923, 1765, 1694, 1456, 1428, 1383, 1237, 990, 813, 742, 656.

Example 2.12

1-Methyl-3-(2-methyl-1H-indol-3-yl)-4-(naphthalen-2-yl)-1H-pyrrole-2,5-dione

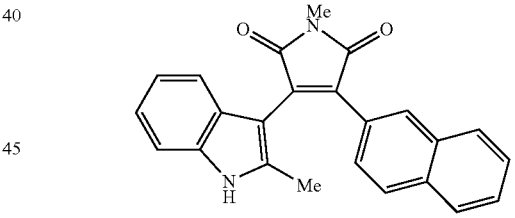

Red crystals; $^1$H NMR (CDCl$_3$) δ 2.09 (s, 3H), 3.24 (s, 3H), 6.95 (ddd, 1H, J~1.04, 7.14, 8.12 Hz), 7.11 (ddd, 1H, J~1.11, 7.13, 8.18 Hz), 7.20 (dd, 1H, J~0.5, 8.12 Hz), 7.25 (dd, 1H, J~<0.5, 8.07 Hz), 7.44 (dd, 1H, J~1.68, 8.58 Hz), 7.48 (m, 2H), 7.59 (br.d, 1H, J~8.71 Hz), 7.74 (m, 1H), 7.83 (m, 1H), 8.33 (br.s, 2H); $^{13}$C NMR (CDCl$_3$) δ 13.7, 24.3, 103.1, 110.5, 120.4, 120.6, 122.1, 125.8, 126.3, 126.8, 127.1, 127.6, 127.7, 127.8, 128.9, 130.0, 133.0, 133.18, 133.22, 133.8, 135.7, 136.9, 171.2, 171.6; GC-MS (EI, 70 eV): m/z (%) 366 (100) [M$^+$]; HRMS (ED: Cacld for C$_{24}$H$_{18}$O$_2$N$_2$: 366.13628; found: 366.13581; IR (ATR, cm$^{-1}$): 3345, 3055, 2946, 1759, 1689, 1425, 1381, 1226, 989, 816, 737, 660.

Example 2.13

3-(2,5-Dimethoxyphenyl)-1-methyl-4-(2-methyl-1H-indol-3-yl)-1H-pyrrole-2,5-dione

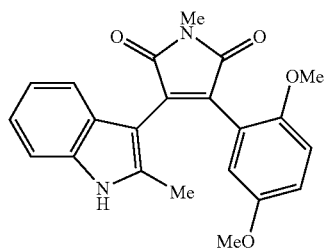 [SMILES: COc1ccc(OC)c(C2=C(c3c(C)[nH]c4ccccc34)C(=O)N(C)C2=O)c1]

Deep orange crystals; $^1$H NMR (CDCl$_3$) δ 2.05 (s, 3H), 3.19 (s, 3H), 3.36 (s, 3H), 3.66 (s, 3H), 6.75 (br.d, 1H, J~8.79 Hz), 6.81 (br.d, 1H, J~2.57 Hz), 6.84 (dd, 1H, J~3.05, 8.80 Hz), 6.94 (ddd, 1H, J~1.13, 7.08, 8.02 Hz), 7.05 (ddd, 1H, J~1.07, 7.15, 8.02 Hz), 7.14 (br.d, 1H, J~8.11 Hz), 7.18 (br.d, 1H, J~7.94 Hz), 8.38 (br.s, 1H); $^{13}$C NMR (CDCl$_3$) δ 13.3, 24.2, 55.78, 55.84, 104.0, 110.2, 112.7, 115.9, 116.2, 119.9, 120.3, 120.6, 121.8, 127.0, 133.3, 135.5, 135.6, 136.6, 151.9 (2C), 153.4 (2C), 171.0, 171.3; GC-MS (EI, 70 eV): m/z (%) 376 (100) [M$^+$]; HRMS (EI): Cacld for C$_{22}$H$_{20}$O$_4$N$_2$: 376.14176; found: 376.14113; IR (ATR, cm$^{-1}$): 3338, 2924, 1750, 1689, 1427, 1383, 1273, 1237, 1212, 1049, 1018, 997, 823, 760, 746, 724, 667.

Example 2.14

1-Methyl-3-(2-methyl-1H-indol-3-yl)-4-(2-(trifluoromethyl)phenyl)-1H-pyrrole-2,5-dione

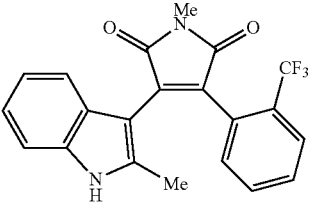 [SMILES: Cc1[nH]c2ccccc2c1C1=C(c2ccccc2C(F)(F)F)C(=O)N(C)C1=O]

Orange crystals; $^1$H NMR (Aceton-d$_6$) δ 2.20 (s, 3H), 3.11 (s, 3H), 6.86 (ddd, 1H, J~1.06, 7.13, 8.07 Hz), 7.00 (ddd, 1H, J~1.16, 7.16, 8.13 Hz), 7.19 (br.d, 1H, J 7.95 Hz), 7.27 (ddd, 1H), 7.37 (m, 1H), 7.55 (m, 2H), 7.76 (m, 1H), 10.55 (br.s, 1H); $^{13}$C NMR (Aceton-d$_6$) δ 13.1, 24.1, 102.3 (d, J=4.55 Hz), 111.2 (d, J=5.13 Hz), 120.0, 120.2, 121.9, 124.9 (q, J=272.93 Hz), 127.7 (q, J=4.42 Hz), 127.9 (d, J=3.68 Hz), 129.6 (q, J=30.37 Hz), 129.9 (d, J=1.79 Hz), 130.0, 132.5 (2C), 135.4, 136.5 (d, J=15.20 Hz), 137.5, 138.4 (d, J=14.52 Hz), 170.87, 170.93; $^{19}$F NMR (CDCl$_3$) δ −57.57 (s); GC-MS (EI, 70 eV): m/z (%) 384 (100) [M$^+$]; HRMS (EI): Cacld for C$_{21}$H$_{15}$O$_2$N$_2$F$_3$: 384.10801; found: 384.10765; IR (ATR, cm$^{-1}$): 3365, 3080, 1768, 1694, 1445, 1385, 1315, 1163, 1118, 1036, 991, 764, 742, 657.

Example 2.15

3-(4-Fluorophenyl)-1-methyl-4-(2-methyl-1H-indol-3-yl)-1H-pyrrole-2,5-dione

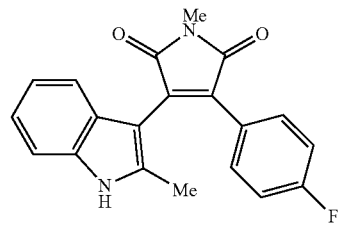 [SMILES: Cc1[nH]c2ccccc2c1C1=C(c2ccc(F)cc2)C(=O)N(C)C1=O]

Orange crystals; $^1$H NMR (CDCl$_3$) δ 2.21 (s, 3H), 3.20 (3, 3H), 6.96 (m, 3H), 7.03 (dd, 1H, J~0.35, 7.75 Hz), 7.12 (ddd, 1H, J~1.24, 6.93, 8.13 Hz), 7.25 (ddd, 1H), 7.59 (ddt, 2H, J~2.90, 5.50, 8.48 Hz), 8.35 (br.s, 1H); $^{13}$C NMR (CDCl$_3$) δ 13.7, 24.2, 102.6, 110.6, 115.4, 115.7, 120.2, 120.6, 122.1, 126.22 (d, J~3.60 Hz), 126.3, 131.4, 131.5, 132.87 (d, J~1.07 Hz), 132.0, 135.8, 136.9, 162.89 (d, J=251.81 Hz), 171.1, 171.5; $^{19}$F NMR (CDCl$_3$) δ −109.8 (s); HRMS (EI): Cacld for C$_{20}$H$_{15}$O$_2$N$_2$F: 334.11121; found: 334.11137; IR (ATR, cm$^{-1}$): 3380, 3042, 1755, 1700, 1600, 1508, 1458, 1427, 1379, 1232, 1159, 996, 841, 813, 750, 731, 657.

Example 2.16

3-(5-Acetyl-2-fluorophenyl)-1-methyl-4-(2-methyl-1H-indol-3-yl)-1H-pyrrole-2,5-dione

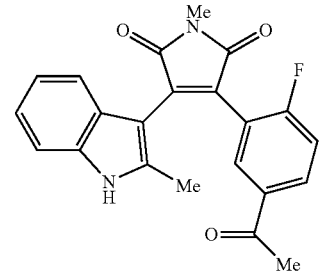 [SMILES: CC(=O)c1ccc(F)c(C2=C(c3c(C)[nH]c4ccccc34)C(=O)N(C)C2=O)c1]

Deep red crystals; $^1$H NMR (Aceton-d$_6$) δ 2.29 (s, 3H), 2.49 (s, 3H), 3.12 (s, 3H), 6.80 (ddd, 1H, J~1.06, 7.15, 8.37 Hz), 7.00 (m, 2H), 7.16 (dd, 1H, J=8.69, 9.51 Hz), 7.30 (dd, 1H, J=0.82, 8.69 Hz), 8.01 (ddd, 1H, J=2.34, 4.90, 8.57 Hz), 8.17 (dd, 1H, J=2.23, 6.79 Hz), 10.65 (br.s, 1H); $^{13}$C NMR (Aceton-d$_6$) δ 13.4, 24.1, 26.3, 103.5, 111.4, 116.6 (d, J=22.4 Hz), 119.9, 120.1 (d, J=16.2 Hz), 120.4, 122.0, 127.4, 128.7 (d, J=2.5 Hz), 131.8 (d, J=9.6 Hz), 133.0 (d, J=4.6 Hz), 134.2 (d, J=3.4 Hz), 136.7, 138.4, 138.9, 163.4 (d, J=259.4 Hz), 170.6, 170.8, 195.9; $^{19}$F NMR (Aceton-d$_6$) δ −102.9 (m); GC-MS (EI, 70 eV): m/z (%) 376 (100) [M$^+$]; HRMS pos. (ESI): Calc for [M+H]$^+$, C$_{22}$H$_{18}$FN$_2$O$_3$: 377.1296; found: 377.1302; HRMS pos. (ESI): Calc for [M+Na]$^+$, C$_{22}$H$_{17}$FN$_2$NaO$_3$: 399.11154; found: 399.11152; IR (ATR, cm$^{-1}$): 3351, 1689, 1645, 1602, 1439, 1386, 1353, 1250, 1223, 828, 778, 742, 630, 568, 436, 408.

Example 2.17

N-(4-(1-Methyl-4-(2-methyl-1H-indol-3-yl)-2,5-dioxo-2,5-dihydro-1H-pyrrol-3-yl)phenyl)acetamide

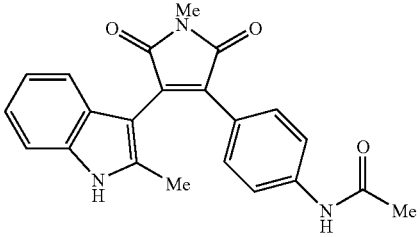 [SMILES: CC(=O)Nc1ccc(C2=C(c3c(C)[nH]c4ccccc34)C(=O)N(C)C2=O)cc1]

Orange crystals; ¹H NMR (Aceton-d₆) δ 2.05 (s, 3H), 2.27 (s, 3H), 3.07 (s, 3H), 6.83 (ddd, 1H, J~0.98, 6.93, 8.06 Hz), 7.00 (d, 1H, J=7.60 Hz), 7.02 (ddd, 1H), 7.32 (ddd, 1H, J~1.00, 2.09, 7.76 Hz), 7.53 (m, 4H), 9.27 (br.s, 1H), 10.59 (br.s, 1H); ¹³C NMR (Aceton-d₆) δ 13.3, 23.8, 24.0, 103.0, 111.3, 118.8 (2C), 120.1, 120.5, 121.8, 125.9, 127.2, 130.6 (2C), 132.6, 133.8, 136.9, 137.9, 140.7, 168.8, 171.4, 171.9; GC-MS (EI, 70 eV): m/z (%) 373 (100) [M⁺]; HRMS pos. (ESI): Calc for [M+H]⁺, C₂₂H₂₀N₃O₃: 374.14992; found: 374.15012; HRMS pos. (ESI): Calc for [M+Na]⁺, C₂₂H₁₉N₃NaO₃: 396.13186; found: 396.13226; IR (ATR, cm⁻¹): 3379, 1675, 1582, 1505, 1424, 1403, 1386, 1365, 1310, 1237, 1179, 851, 815, 750, 653, 585, 567, 556, 532, 434, 379.

Example 3: Preparation 3—General Procedure for Preparation of Compounds of Formula (II) and (III) and Specific Compounds Step 1. The mixture of compound of formula (I) (1 mmol) wherein X is N—R¹, and 100 ml of 10% aq KOH was heated at 140° C. until the mixture become homogenous (10 to 30 min, TLC control). Then the solution was cooled and acidified with 2N aq HCl, until precipitate was formed, which was collected, dried and recrystallized to give nearly quantitatively cyclic anhydride of formula (II).

Step 2. Compound of formula (II) (1 mmol) was heated with ammonium acetate (100 mmol) at 140° C. until the mixture become homogenous (TLC control). The mixture was cooled down, water was added, and the mixture was extracted with ethyl acetate. The combined organics were washed with water, dried over Na₂SO₄ and concentrated. The crude material was crystallized from ether. The product of formula (III) was isolated by column chromatography in heptane/ethyl acetate.

Example 3.18

3-(2-Methyl-1H-indol-3-yl)-4-phenylfuran-2,5-dione

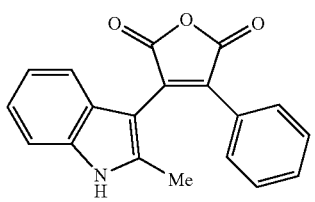 [SMILES: Cc1[nH]c2ccccc2c1C1=C(c2ccccc2)C(=O)OC1=O]

Red crystals; ¹H NMR (Aceton-d₆) δ 2.31 (s, 3H), 6.86 (ddd, 1H, J 1.03, 7.06, 8.08 Hz), 7.02 (ddd, 1H), 7.07 (ddd, 1H, J~1.14, 7.17, 8.21 Hz), 7.36 (m, 4H), 7.60 (m, 2H), 10.83 (br.s, 1H); ¹³C NMR (Aceton-d₆) δ 13.4, 102.2, 111.6, 120.6 (2C), 122.4, 126.7, 128.9 (2C), 129.9 (2C), 130.2, 130.4, 134.9, 136.1, 136.9, 139.7, 166.1, 166.3; GC-MS (EI, 70 eV): m/z (%) 303 (52) [M⁺]; HRMS (EI): Calc for C₁₉H₁₃O₃N: 303.08899; found: 303.08861; IR (ATR, cm⁻¹): 3350, 2921, 2852, 1825, 1749, 1618, 1456, 1423, 1252, 902, 741, 726, 693, 671, 635, 622, 564, 531.

Example 3.19

3-(2-Methyl-1H-indol-3-yl)-4-phenyl-1H-pyrrole-2,5-dione

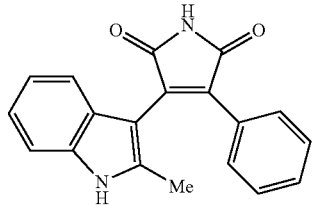 [SMILES: Cc1[nH]c2ccccc2c1C1=C(c2ccccc2)C(=O)NC1=O]

Red crystals; ¹H NMR (Aceton-d₆) δ 2.24 (s, 3H), 6.83 (ddd, 1H, J~1.01, 7.08, 8.01 Hz), 7.02 (ddd, 1H), 7.03 (d, 1H, J=7.58 Hz), 7.27 (m, 3H), 7.31 (ddd, 1H), 7.54 (m, 2H), 9.83 (br.s, 1H), 10.56 (br.s, 1H); ¹³C NMR (Aceton-d₆) δ 13.2, 102.8, 111.2, 120.1, 120.5, 121.8, 127.3, 128.6 (2C), 129.3, 130.0 (2C), 131.3, 134.8, 134.9, 136.8, 138.0, 171.7, 172.2; GC-MS (EI, 70 eV): m/z (%) 302 (100) [M⁺]; HRMS (EI): Calc for C₁₉H₁₄O₂N₂: 302.10498; found: 302.105426; IR (ATR, cm⁻¹): 3379, 3205, 3065, 2917, 2764, 1764, 1704, 1598, 1451, 1423, 1335, 1289, 1278, 1227, 1013, 993, 770, 754, 729, 719, 690.

Example 3.20

3-(2-Methyl-1H-indol-3-yl)-4-(naphthalen-2-yl)furan-2,5-dione

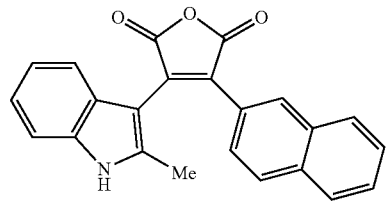 [SMILES: Cc1[nH]c2ccccc2c1C1=C(c2ccc3ccccc3c2)C(=O)OC1=O]

Orange crystals; ¹H NMR (CDCl₃) δ 2.30 (s, 3H), 6.81 (ddd, 1H), 7.05 (ddd, 2H), 7.37 (ddd, 1H), 7.53 (m, 3H), 7.75 (d, 1H, J~8.62 Hz), 7.87 (m, 2H), 8.36 (s, 1H), 10.86 (s, 1H); ¹³C NMR (CDCl₃) δ 13.3, 102.5, 111.6, 120.6, 120.7, 122.4, 126.0, 126.9, 127.2, 127.7, 128.16, 128.24, 128.4, 129.3, 130.7, 133.5, 134.1, 134.7, 136.1, 136.9, 139.9, 166.1, 166.4; MS (EI): m/z (%) 353 (650) [M⁺]; HRMS pos. (ESI): Calc for [M+H]⁺, C₂₃H₁₆NO₃: 354.11247; found: 354.11221; HRMS pos. (ESI): Calc for [M+Na]⁺, C₂₃H₁₅NNaO₃: 376.09441; found: 376.09419; IR (ATR, cm⁻¹): 3366, 2926, 1757, 1460, 1428, 1259, 1242, 1222, 1158, 910, 784, 766, 737, 590, 554, 475.

Example 3.21

3-(2-Methyl-1H-indol-3-yl)-4-(naphthalen-2-yl)-1H-pyrrole-2,5-dione

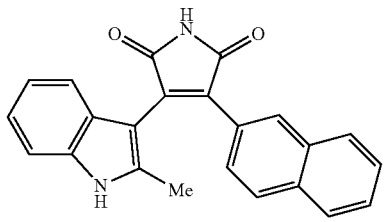 [SMILES: Cc1[nH]c2ccccc2c1C1=C(c2ccc3ccccc3c2)C(=O)NC1=O]

Orange crystals; $^1$H NMR (Aceton-$d_6$) δ 2.24 (s, 3H), 6.77 (ddd, 1H, J~1.04, 7.12, 8.07 Hz), 7.00 (ddd, 1H, J 1.15, 7.10, 8.07 Hz), 7.08 (d, 1H, J=8.0 Hz), 7.33 (ddd, 1H, J=0.85, 8.08), 7.48 (m, 3H), 7.66 (d, 1H, J=8.8 Hz), 7.80 (m, 1H), 7.84 (m, 1H), 8.30 (d, 1H, J=0.72 Hz), 9.90 (br.s, 1H), 10.60 (br.s, 1H); $^{13}$C NMR (Aceton-$d_6$) δ 13.3, 103.1, 111.3, 120.2, 120.5, 121.9, 126.6, 126.9, 127.5 (2C), 128.0, 128.1, 128.9, 129.1, 130.4, 133.6, 133.7, 134.5, 135.0, 136.8, 138.3, 171.7, 172.3; MS (EI): m/z (%) 352 (100) [M$^+$]; HRMS (EI): Calc for $C_{23}H_{16}O_2N_2$: 352.12063; found: 352.120553; IR (ATR, cm$^{-1}$): 3379, 3209, 3062, 2959, 2925, 2738, 1762, 1702, 1621, 1457, 1426, 1329, 1290, 1222, 1034, 993, 858, 826, 786, 754, 742, 715, 670, 662.

Example 3.22

3-(4-Acetylphenyl)-4-(2-methyl-1H-indol-3-yl)furan-2,5-dione

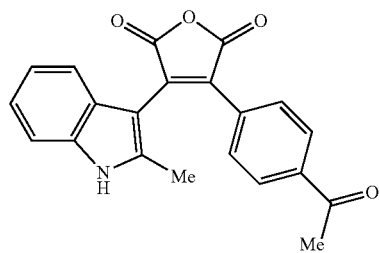 [SMILES: CC(=O)c1ccc(C2=C(c3c(C)[nH]c4ccccc34)C(=O)OC2=O)cc1]

Red-orange crystals; $^1$H NMR (CDCl$_3$) δ 2.33 (s, 3H), 2.56 (s, 3H), 6.86 (ddd, 1H, J~1.0, 7.04, 8.08 Hz), 6.99 (br. d, 1H, J~8.0 Hz), 7.07 (ddd, 1H, J~1.22, 7.02, 8.12 Hz), 7.34 (ddd, 1H, J~0.80, 0.84, 8.10), 7.72 (ddd, 2H), 7.94 (ddd, 2H), 10.98 (br.s, 1H); $^{13}$C NMR (CDCl$_3$) δ 13.5, 26.4, 102.3, 111.7, 120.6, 120.8, 122.5, 126.5, 128.6 (2C), 130.1 (2C), 133.3, 134.5, 136.9, 137.5, 138.0, 140.4, 165.9, 166.0, 197.2; GC-MS (EI, 70 eV): m/z (%) 345 (87) [M$^+$]; HRMS (EI): Calc for $C_{21}H_{15}O_4N$: 345.09956; found: 345.09942; IR (ATR, cm$^{-1}$): 3233, 2921, 2852, 1759, 1671, 1460, 1252, 1186, 1112, 924, 831, 747, 731, 628, 591, 578, 516, 456, 434, 416.

Example 3.23

3-(4-Acetylphenyl)-4-(2-methyl-1H-indol-3-yl)-1H-pyrrole-2,5-dione

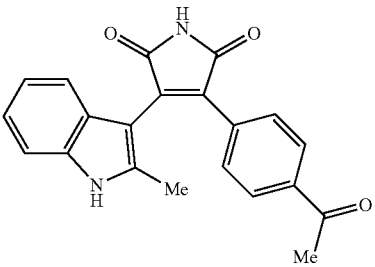 [SMILES: CC(=O)c1ccc(C2=C(c3c(C)[nH]c4ccccc34)C(=O)NC2=O)cc1]

Orange crystals; $^1$H NMR (Aceton-$d_6$) δ 2.28 (s, 3H), 2.53 (s, 3H), 6.82 (ddd, 1H, J~1.03, 7.07, 8.03 Hz), 6.99 (br. d, 1H, J~7.40 Hz), 7.02 (ddd, 1H, J~1.12, 7.07, 8.11 Hz), 7.33 (ddd, 1H, J~0.81, 0.95, 8.08), 7.66 (ddd, 2H), 7.87 (ddd, 2H), 9.93 (br.s, 1H), 10.67 (br.s, 1H); $^{13}$C NMR (Aceton-$d_6$) δ 13.4, 26.4, 102.8, 111.4, 120.3, 120.5, 122.0, 127.1, 128.4 (2C), 130.2 (2C), 133.3, 135.9, 136.3, 136.9, 137.2, 138.7, 171.4, 171.8, 197.2; GC-MS (EI, 70 eV): m/z (%) 344 (100) [M$^+$]; HRMS (ED: Calc for $C_{21}H_{16}O_3N_2$: 344.11554; found: 344.11495; IR (ATR, cm$^{-1}$): 3343, 3296, 3057, 1757, 1699, 1676, 1428, 1343, 1262, 1230, 740, 666, 638, 595, 460, 409.

Example 3.24

3-(4-Acetylphenyl)-4-(1,2-dimethyl-1H-indol-3-yl)-1-methyl-1H-pyrrole-2,5-dione

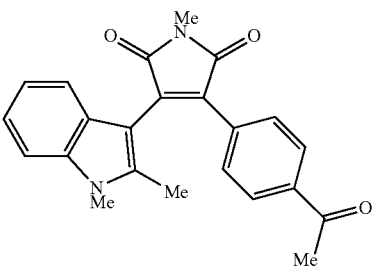 [SMILES: CC(=O)c1ccc(C2=C(c3c(C)n(C)c4ccccc34)C(=O)N(C)C2=O)cc1]

Dark red crystals; $^1$H NMR (DMSO-$d_6$) δ 2.18 (s, 3H), 2.52 (s, 3H), 3.03 (s, 3H), 3.71 (s, 3H), 6.84 (ddd, 1H), 6.93 (br.d, 1H, J 7.54 Hz), 7.08 (ddd, 1H, J~1.06, 7.08, 8.14 Hz), 7.45 (br.d, 1H, J 8.25 Hz), 7.56 (br.d, 2H, J 8.50 Hz), 7.86 (br.d, 2H, J 8.50 Hz); $^{13}$C NMR (DMSO-$d_6$) δ 12.3, 24.2, 26.8, 29.9, 101.3, 109.9, 119.7, 119.9, 121.3, 125.1, 128.1 (2C), 129.3 (2C), 131.6, 134.6, 135.1, 136.2, 137.1, 139.6, 170.4, 170.7, 197.5; GC-MS (EI, 70 eV): m/z (%) 372 (100) [M$^+$]; HRMS pos. (ESI): Calc for [M+H]$^+$, $C_{23}H_{21}N_2O_3$: 373.15467; found: 373.15473; IR (ATR, cm$^{-1}$): 3433, 2915, 1759, 1680, 1599, 1433, 1404, 1382, 1359, 1265, 1240, 957, 849, 829, 749, 738, 726, 595, 546, 439.

Example 3.25

3-(4-Acetylphenyl)-1-methyl-4-(1H-pyrrolo[2,3-b]pyridin-3-yl)-1H-pyrrole-2,5-dione

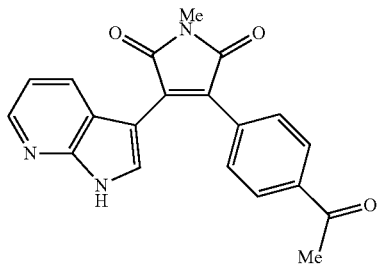 [SMILES: CC(=O)c1ccc(C2=C(c3c[nH]c4ncccc34)C(=O)N(C)C2=O)cc1]

Yellow crystals; $^1$H NMR (DMSO-d$_6$) δ 2.57 (s, 3H), 3.04 (s, 3H), 6.66 (dd, 1H, J~0.89, 8.00 Hz), 6.80 (dd, 1H, J~4.74, 7.96 Hz), 7.55 (br.d, 2H, J~8.27 Hz), 7.93 (br.d, 2H, J~8.20 Hz), 8.11 (s, 1H), 8.18 (br.d, 2H, J~3.70 Hz), 12.55 (br.s, 1.H); $^{13}$C NMR (DMSO-d$_6$) δ 24.1, 26.8, 102.8, 116.28, 116.34, 128.0 (2C), 128.4, 129.1, 129.9 (2C), 131.8, 132.5, 134.8, 136.5, 143.7, 149.0, 170.6, 170.8, 197.5; GC-MS (EI, 70 eV): m/z (%) 345 (100) [M$^+$]; HRMS pos. (ESI): Calc for [M+H]$^+$, C$_{20}$H$_{16}$N$_3$O$_3$: 346.11862; found: 346.11828; IR (ATR, cm$^{-1}$): 3025, 2873, 2817, 1756, 1695, 1677, 1440, 1421, 1385, 1289, 1269, 1229, 1090, 814, 776, 750, 645, 596, 514.

Example 4: GSK3β Kinase Activity Assay

The kinase activity assay was performed as previously described by Schmole et. al., 2010 (Schmole et al., 2010, Novel indolylmaleimide acts as GSK-3beta inhibitor in human neural progenitor cells. Bioorganic medicinal chemistry, 18, 6785-95). Briefly, recombinant human GSK3β (Biomol, Hamburg, Germany) was incubated with its substrate phospho glycogen synthase peptide 2 (pGS2) (Millipore, Billerica, USA), ATP (Cell Signaling, Frankfurt am Main, Germany) and different concentrations of PDA-66 for 30 min at 30° C. After addition of Kinase-Glo (Promega, Mannheim, Germany) and 10 min of incubation at room temperature the luminescence signal was measured with a Glomax 96 microplate reader (Promega). More specifically, recombinant human GSK3β was incubated with pGS2, ATP and different concentrations of PDA-66. Kinase activity was significantly inhibited at concentrations between 0.25 μM and 1 μM of PDA-66. Results are displayed as the mean±SD of two independent experiments. In each experiment the concentrations of PDA-66 and the control were tested with 8 replicates. * Significant treatment effect vs. DMSO control, α=0.05.

PDA-66 Inhibits Kinase Activity of Recombinant GSK3β

The effect of PDA-66 on the enzyme activity of GSK3β was determined by incubation of the enzyme with a specific substrate, PDA-66 and ATP. With growing inhibitory effect there is more ATP present after the incubation. In a second step remaining ATP is converted to a luminescence signal, which is inversely proportional to the enzyme activity. The analysis of kinase activity of GSK3β in our study shows a bell shaped dose response relationship (FIG. 1). The incubation with 0.25-1 μM of PDA-66 led to significant increase of luminescence signal and therefore an inhibition of the enzyme, whereas 10 μM seems to enhance enzyme activity.

Example 5: Treatment of ALL Cell Lines with PDA-66

The human B-ALL cell lines SEM, RS4;11 and the human T-ALL cell lines Jurkat and Molt-4 were purchased from DSMZ (Germany) and cultured according to manufacturer's protocol. The corresponding medium was supplemented with 10% heat-inactivated fetal bovine serum (PAA, Pasching, Austria) and 1% penicillin and streptomycin (Biochrom AG, Berlin, Germany). The Molt-4 cells were cultured with medium supplemented with 20% heat-inactivated fetal bovine serum. All cells were maintained at 37° C. in 5% CO$_2$. Cells (5×10$^5$/well) were seeded in 24 well plates (Nunc, Langenselbold, Germany) and incubated for up to 72 h with PDA-66. Treated cells were harvested after 4, 24, 48 and 72 h and used for further analyses.

Cell counts were determined using the trypan blue staining. Metabolic activity was analyzed by using tetrazolium compound WST-1 (Roche, Mannheim, Germany). In brief, triplicates of cells (5×10$^4$/well) were seeded in 96 well plates, treated with PDA-66 and incubated with 15 μl WST-1 for up to 4 h. The mitochondrial dehydrogenases reduce WST-1 to soluble formazan and cause a change of color, which correlates with the amount of metabolically active cells. Absorbance at 450 nm and a reference wavelength at 620 nm were determined by an ELISA Reader (Anthos, Krefeld, Germany). The absorbance of culture medium with supplemented WST-1 in the absence of cells was used as background control.

PDA-66 Inhibits Proliferation and Metabolic Activity of ALL Cells

Figure 2:
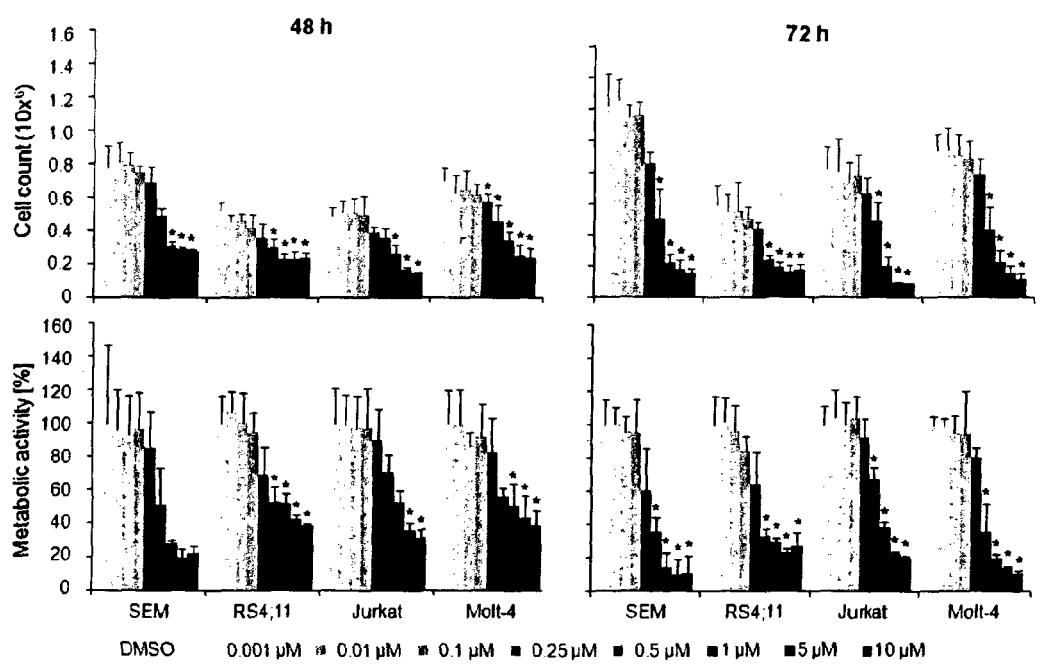
FIG. 2 is a set of bar diagrams showing the impact of compound PDA-66 on cell proliferation and metabolic activity of SEM cells, RS4;11 cells, Jurkat cells and Molt-4 cells.

The influence of PDA-66 on proliferation in ALL cell lines SEM, RS4;11, Jurkat and Molt-4 was analyzed by incubation with different concentrations of the drug (0.001 μM to 10 μM). Metabolic activity was determined using WST-1 assay. The proliferation and metabolic activity of all cell lines was suppressed significantly at higher concentrations. Results are displayed as the mean±SD of three independent experiments. * Significant treatment effect vs. DMSO control, α=0.05. Results are summarized in FIG. 2, whereby the individual nine bars for each set of experiments represent, from left to right, DMSO, 0.001 μM, 0.01 μM, 0.1 μM, 0.25 μM, 0.5 μM, 1.0 μM, 5 μM and 10 μM. After 48 h of incubation an inhibition of proliferation could be observed, but was more distinct after 72 h. There was a significant inhibition after 72 h in all cell lines at a concentration of 0.5 μM PDA-66.

Similar results could be detected in WST-1 assay. After 72 h of incubation the metabolic activity was significantly decreased in all cell lines at a concentration of 0.5 μM PDA-66. At this concentration the metabolic activity decreased to 35.7±8.3% in SEM, 33.3±4.4% in RS4;11, 66.7±8% in Jurkat and 35.5±17% in Molt-4 cells compared to control cells treated with DMSO. In WST-1 assay the IC50 concentrations for PDA-66 in all four cell lines where determined (Table 1). The IC50 values range from 0.41 μM in SEM cells to 1.28 μM in Jurkat cells after 72 h of incubation.

The incubation of ALL cell lines with higher dosages of PDA-66 (0.5 μM or more) led to a decrease in cell numbers i.e. below the amount of seeded cells (5×10$^5$). This result indicates not only an influence on proliferation but also an induction of cell death.

Example 6: May Grunwald-Giemsa Staining

Cytospins of SEM and Jurkat cells were stained with May Grunwald-Giemsa Staining after 48 h of incubation with 1 μM PDA-66 and DMSO, respectively After treatment with 1 µM PDA-66 3×10⁴ cells were brought onto object slides with Cytospin 3 centrifuge (Shandon, Frankfurt/Main, Germany). Subsequently cells were stained using May-Grunwald-Giemsa staining. Briefly, slides were incubated in May-Grunwald solution (Merck, Darmstadt, Germany) for 6 min, then washed with tap water, incubated in Giemsa solution (Merck, Darmstadt, Germany) for 20 min and washed in tap water again. After letting the slides dry the cells were analyzed by Nikon Eclipse E 600 light microscope and pictures were taken with NIS Elements software (Nikon, Düsseldorf, Germany).

PDA-66 Influences Morphology of ALL Cells

Figure 3:
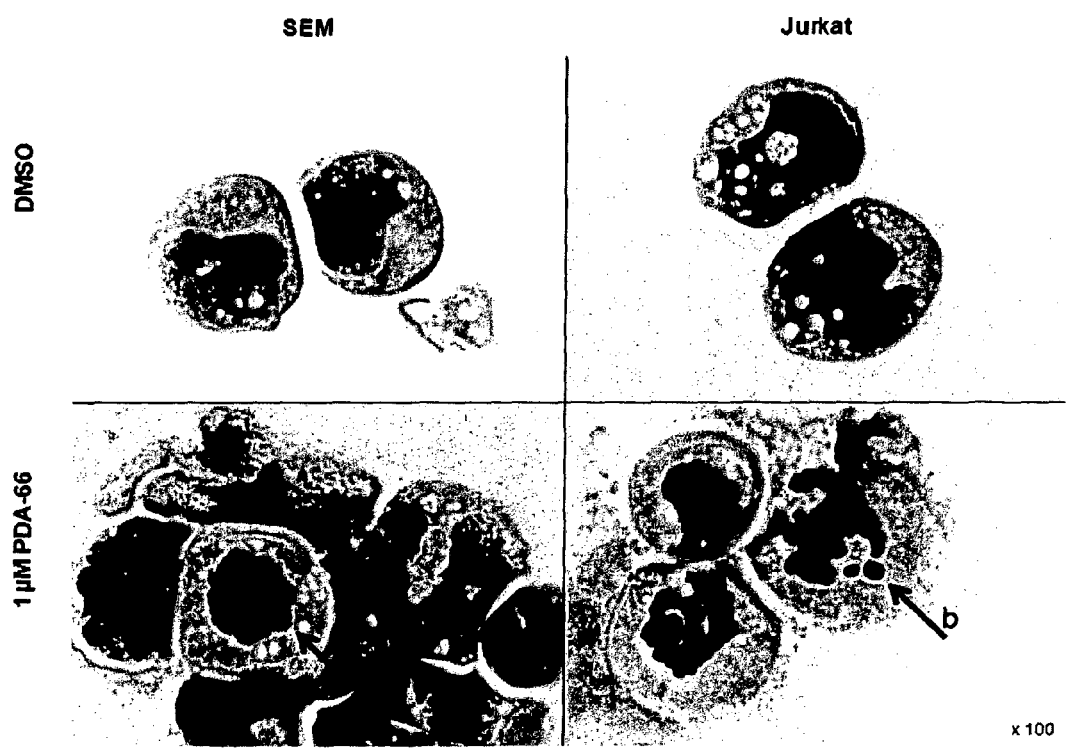
FIG. 3 is a set of light microscopic pictures indicating the effect of compound PDA-66 and DSMO on SEM cells and Jurkat cells.

The analysis via light microscopy showed an influence on the morphology of all four cell lines. After treatment an increased amount of cells with chromatin condensation (black arrow a in FIG. 3) and karyorrhexis (black arrow b in FIG. 3) could be observed along with more cell debris. In contrast to DMSO treated control cells the incubation of PDA-66 led to condensation of chromatin in the nucleus, karyorrhexis and an increasing amount of vacuoles and cell debris after 48 h of treatment (FIG. 3). Condensated chromatin might hint to induction of apoptosis on the one hand or cell cycle arrest on the other hand.

Example 7: Cell Cycle Analysis

After treatment cells were harvested and washed twice in PBS. Cells were fixed with 70% ethanol and incubated with 1 mg/ml Ribonuclease A (Sigma-Aldrich, St. Louis, USA) for 30 min at 37° C. After washing the cells twice in PBS, they were stained with PI (50 µg/ml) and DNA content was determined by flow cytometry. All cell lines were incubated with PDA-66 and cell cycle distribution was determined using Propidium iodide staining.

Figure 4:
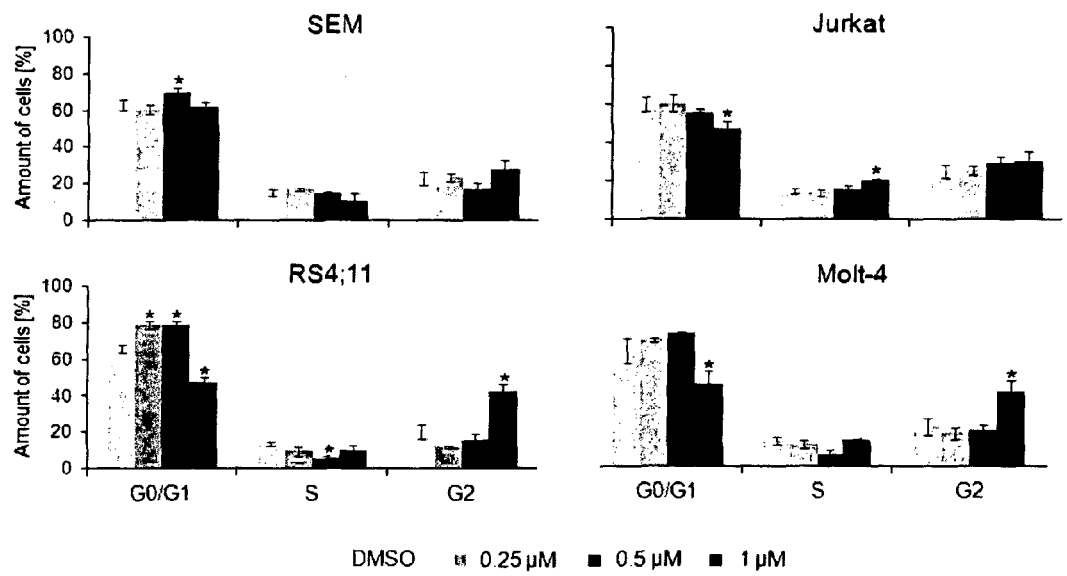
FIG. 4 is a set of bar diagrams showing the impact of compound PDA-66 on cell cycle distribution of SEM cells, RS4;11 cells, Jurkat cells and Molt-4 cells.

The treatment with PDA-66 influenced the four cell lines differently. Results are displayed in FIG. 4, whereby the individual four bars for each set of experiments represent, from left to right, DMSO, 0.25 µM, 0.5 µM and 1.0 µM. G2 arrest could be detected in RS4;11 and Molt-4 cells after 48 h of treatment. Treatment of Jurkat cells induced a decrease of cells in G0/G1 phase in favor of cells in S phase. Results are displayed as the mean±SD of three independent experiments. * Significant treatment effect vs. DMSO control, α=0.05.

SEM cells showed a significant increase in the amount of cells in G0/G1 after 48 h of incubation with 0.5 µM (DMSO control: 62.8±2.8%; 0.5 µM PDA-66: 69.3±2.7%) whereas 1 µM did not affect the cell cycle significantly. RS4;11 and Molt-4 cells were characterized by a significant G2 arrest 48 h after treatment with 1 µM PDA-66. The amount of RS4;11 and Molt-4 cells in G2 phase increased from 20.1±3.9% and 21.9±4.9% after incubation with DMSO to 42.1±4.4% and 41.0±5.8% after PDA-66 treatment. This was associated with a significant decrease in G0/G1 phase (RS4;11 and Molt-4: 65.7±2.1% and 63.7±6.6% in control; 47.3±2.7% and 45.0±7.3% after treatment with 1 µM PDA-66). On the other hand smaller dosages led to significant increase of cells in G0/G1 phase. Jurkat cells showed a significant decrease in G0/G1 phase (from 60.0±3.7% in control to 47.3±4.3% with PDA-66) and an increase in S phase (from 14.6±1.5% in control to 20.0±1.1% with PDA-66) after incubation with 1 µM PDA-66.

Example 8: Analyses of Apoptosis and Necrosis

Apoptosis and necrosis were analyzed by staining the cells with Annexin V FITC (BD Biosciences, Heidelberg, Germany) and propidium iodide (PI) (Sigma Aldrich, St. Louis, USA). Results were assessed by flow cytometry.

(A) Cells were treated with PDA-66 for up to 72 h and stained with Annexin V FITC and Propidium iodide (PI). Rates of early apoptotic (FITC⁺, PI⁻) and late apoptotic and necrotic (FITC⁺, PI⁺) cells were measured by flow cytometry. Significant induction of apoptosis could be observed in all cell lines after 48 h of incubation as well as tendential induction of necrosis at both points of time. Results are displayed as the mean±SD of three independent experiments. * Significant treatment effect vs. DMSO control, α=0.05.

(B) Induction of apoptosis was confirmed by Western blot. Cells were treated with different concentrations of PDA-66 and total cell lysates (25 µg) were analyzed by Western blot to detect cleavage of Caspase 3, 7 and PARP. GAPDH was used as loading control. Exemplary results of SEM cells are displayed.

More specifically, 5×10⁵ cells were harvested and washed twice (180 g, 10 min, 4° C.) with PBS. After resuspending the cells in 100 µl of binding buffer (1×) 4 µl of Annexin V FITC were added and incubated for 15 min at room temperature. Following addition of 400 µl binding buffer for a final volume of 500 µl the cells were stained with PI (0.6 µg/ml) immediately before measurement. As controls unstained and single stained cells were included in each experiment. Measurements were performed using FACSCalibur (Becton and Dickinson, Heidelberg, Germany) and data analyses were carried out with CellQuest software (Becton and Dickinson, Heidelberg, Germany).

PDA-66 Induces Apoptosis

Additionally, the effect of PDA-66 on apoptosis was determined by and western blot. For protein extraction cells were washed twice in PBS and lysed with RIPA buffer (50 mM Tris HCl pH 7.4; 150 mM NaCl; 0.1% SDS and 1% NP40) including protease and phosphatase inhibitors (Roche Applied Science, Mannheim, Germany). Samples were incubated for 20 min at 4° C. and frozen at −20° C. Cell extracts were thawed and centrifuged at 12000 g for 10 min at 4° C. Total protein concentration of supernatants was determined using Bio-Rad Protein Assay (Bio-Rad, München, Germany).

Equal amounts of protein samples were separated by SDS-polyacrylamid gel (8% or 15%) electrophoresis and transferred onto a PVDF membrane (Amersham Biosciences, Buckinghamshire, UK). Membranes were blocked in 5% milk or 5% BSA and incubated at 4° C. overnight with the following polyclonal antibodies: rabbit anti-cleaved caspase 3, rabbit anti-caspase 3, rabbit anti-cleaved PARP, rabbit anti-cleaved caspase 7, rabbit anti-caspase 7 (all Cell Signaling Frankfurt/Main, Germany. Blots were incubated with mouse anti-GAPDH (Invitrogen, Carlsbad, USA) as loading control. Specific horseradish peroxidase-conjugated secondary antibodies (anti-mouse or anti-rabbit) were used. Signals were detected with ECL Plus reagent (Amersham Biosciences; Buckinghamshire, UK) and a CCD camera (Kodak Digital Science Image Station 440CF, Rochester, USA).

After 48 h of incubating the cells with 1 µM PDA-66 all cell lines showed a significant increase in apoptosis compared to control cells (SEM: 2.1±0.9% to 10.5±1.3%; RS4;11: 2.5±0.7% to 7.4±1.1%; Jurkat: 3.8±0.6% to 8.3±1.9%; Molt-4: 3.7±1.2% to 16.3±5.1%). After 72 h a similar tendency could be observed, but only deviations in SEM and Molt-4 cells where significant (SEM: 1.3±0.4% to 5.6±1.6%; RS4;11: 2.1±0.9% to 6.4±3.6%; Jurkat: 4.7±1.9% to 6.1±0.7%; Molt-4: 4.9±1.9% to 20.1±6.6%).

All cells showed a tendential increase in necrosis after 48 and 72 h of incubation with 1 µM PDA-66. After 72 h of incubation necrosis rate rose in SEM cells from 3.1±1.6% to 27.8±5.81%, in RS4;11 cells from 6.1±0.8% to 26.5±10.2%, in Jurkat cells from 5.7±3.5% to 28.0±13.4% and in Molt-4 cells from 11.7±3.6% to 46.7±15.6% (FIG. 5A, whereby the individual four bars for each set of experiments represent, from left to right, DMSO, 0.25 µM, 0.5 µM and 1.0 µM).

Figure 5:
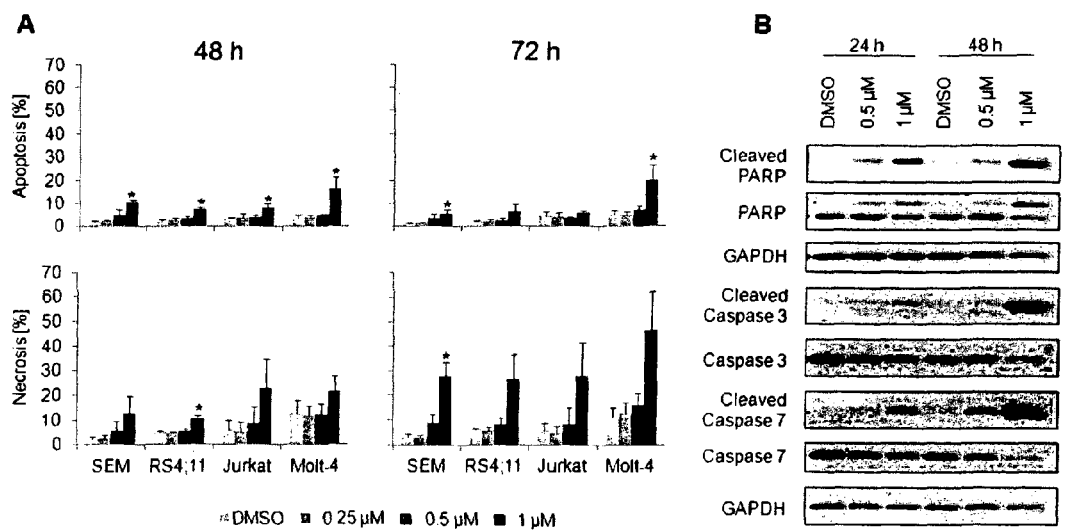
FIG. 5A is a set of bar diagrams showing the impact of compound PDA-66 on apoptosis and necrosis of SEM cells, RS4;11 cells, Jurkat cells and Molt-4 cells.
FIG. 5B shows the result of a Western blot analysis of the effect of compound PDA-66 on cleavage of Caspase 3, 7 and PRAP.

Analysis via Western blot showed an apoptosis induction in all cell lines. Treatment with PDA-66 induced cleavage of caspases 3 and 7 and PARP 48 h after addition of PD066. In FIG. 5B results of SEM cells are displayed exemplarily.

Example 9: Influence on PI3K/Akt and Wnt-Pathway

After treatment with PDA-66 and DMSO, respectively, cells were lyzed and protein expression analyzed with Western blot.

Protein extraction and Western blot was performed as described above. Following polyclonal antibodies were used: rabbit anti-cleaved caspase 3, rabbit anti-caspase 3, rabbit anti-cleaved PARP, rabbit anti-PARP, rabbit anti-cleaved caspase 7, rabbit anti-caspase 7, rabbit anti-pAkt-Thr308, rabbit anti-pAktSer473, rabbit anti-Akt, rabbit anti-β-catenin, rabbit anti-pGSK3βSer9, rabbit anti-GSK3β, rabbit anti-p4EBP-1Ser65 and rabbit anti-4EBP-1 (all Cell Signaling Frankfurt/Main, Germany). Blots were incubated with mouse anti-GAPDH antibody (Invitrogen, Carlsbad, USA) as loading control.

PDA-66 Influences Protein Expression of 4EBP-1, but not β-Catenin or GSK3β

To characterize the effects of PDA-66 on PI3K/Akt and Wnt/β-catenin pathway we performed Western blot analysis. As may be taken from FIG. 6A, no influence on expression of total GSK3β and the total form of Akt could be noticed. A small decrease of pGSK3βSer9 was observed, but no influence on the amount of β-catenin. A slight increase of pAktThr308 was not confirmed by an increase of pAktSer473. Exemplary results of SEM cells are displayed. As may be taken from FIG. 6B, in SEM and RS4;11 cells a decrease of 4 EBP-1 and p4EBP-1Ser65 was detectable, in contrast Molt-4 cells showed an increased expression of p4EBP-1Ser65 after PDA-66 treatment.

Figure 6:
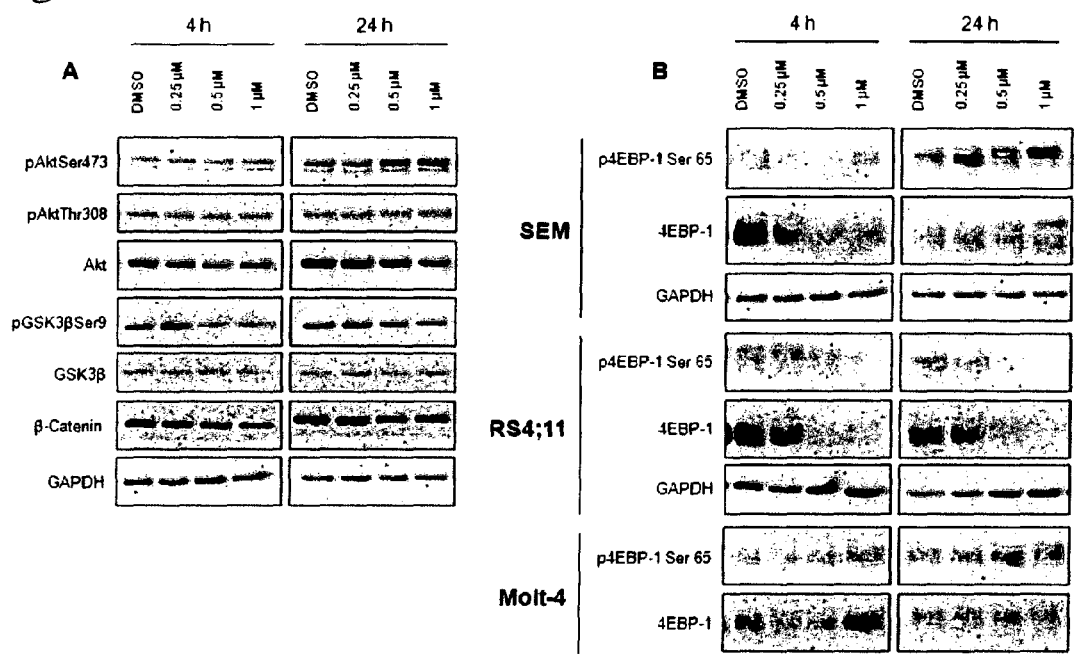
FIG. 6A shows the result of a Western blot analysis of the effect of compound PDA-66 on the expression of pAkt-Ser473, pAktThr308, Akt, pGSK3βSer9, β-Catenin and GAPDH.
FIG. 6B shows the result of a Western blot analysis of the effect of compound PDA-66 on the expression of p4EBP-1Ser65, 4EBP1 and GAPDH in SEM cells, RS4;11 cells and Molt-4 cells.
FIG. 6C shows Table 1 indicating IC50 concentrations of compound PDA-66 in SEM cells, RS4;11 cells, Jurkat cells and Molt-4 cells.

More specifically, the incubation with PDA-66 showed no influence on the expression of β-catenin, total GSK3β and total Akt (FIG. 6). However, an increase of pAktThr308 could be detected in SEM and Jurkat cells after an incubation of 24 h, which was not confirmed by a rise of pAktSer473. Furthermore, in SEM cells a slight decrease of pGSK3βSer9 was observed after 4 h. However, no influence on the total form of β-catenin was detectable. This would not account for an increase of GSK3β activation. Nevertheless, there was an influence of PDA-66 on the expression of 4EBP-1 and p4EBP-1Ser65. SEM, RS4;11 and Jurkat cells showed a decrease of the phosphorylated as well as the total form of 4EBP-1 after an incubation of 4 and 24 h. In contrast, Molt-4 cells displayed an increase of the phosphorylated form to these points of time.

The features of the present invention disclosed in the specification, the claims, the sequence listing and/or the drawings may both separately and in any combination thereof be material for realizing the invention in various forms thereof.

The invention claimed is:

1. A method for arresting or reducing the development of leukemia or the clinical symptoms of leukemia or causing regression of leukemia or the clinical symptoms of leukemia, wherein the method comprises administering to a subject in need thereof a therapeutically effective amount of a compound of formula (I):

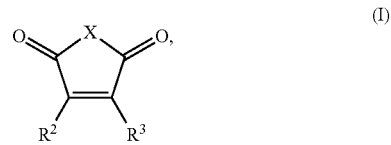

a pharmaceutically acceptable salt thereof, a hydrate thereof, a solvate thereof, a metabolite thereof or a prodrug thereof;
wherein
X is selected from the group consisting of N—$R^1$ and O;
$R^1$ is alkyl or hydrogen;
$R^2$ is indolyl or substituted indolyl; and
$R^3$ is aryl or substituted aryl, wherein the substituted aryl consists of one, two or three substituents, wherein each and any of the substituents is individually and independently selected from the group consisting of fluoro, chloro, methyl, trifluoromethyl, vinyl, acetyl, acetamido, formyl, ethoxycarbonyl and dimethylamidocarbonyl.

2. The method of claim 1, wherein
$R^2$ comprises one, two, three, four, five or six substituents, whereby each and any of the substituents is individually and independently selected from the group comprising halogen, alkyl, alkenyl, alkynyl, acyl, formyl, cycloalkyl, aryl, haloalkyl, polyfluoroalkyl, alkylthio, arylthio, monoalkylamino, dialkylamino, monoarylamino, diarylamino, alkylarylamino, alkylimido, hydroxy, alkoxy, aryloxy, carboxyl, alkoxycarbonyl, aryloxycarbonyl, cyano, amino, amido, acylamino, nitro, alkylsulfinyl, arylsulfinyl, alkyl sulfonyl, aryl sulfonyl, alkylsulfinamido, arylsulfinamido, alkylsulfonamido and arylsulfonamido.

3. The method of claim 1, wherein
X is N—R', and wherein
$R^1$ is selected from the group consisting of alkyl and hydrogen.

4. The method of claim 3, wherein
$R^1$ is selected from the group consisting of methyl, butyl and hydrogen.

5. The method of claim 1, wherein X is O.

6. The method of claim 1, wherein
$R^3$ is selected from the group consisting of monocyclic aryl, substituted monocyclic aryl, bicyclic aryl, and substituted bicyclic aryl.

7. The method of claim 6, wherein
$R^3$ is selected from the group consisting of phenyl, substituted phenyl, naphthenyl, and substituted naphthenyl.

8. The method of claim 7, wherein each and any of the substituents is individually and independently selected from the group consisting of fluoro, chloro, methyl, trifluoromethyl, vinyl, acetyl, acetamido, methoxy, formyl, ethoxycarbonyl and dimethylamidocarbonyl.

9. The method of claim 8, wherein
$R^3$ is selected from the group consisting of phenyl and substituted phenyl, wherein substituted phenyl is phenyl consisting of one, two or three substituents, wherein each and any of the substituents is individually and independently selected from the group consisting of fluoro, chloro, methyl, trifluoromethyl, vinyl, acetyl, acetamido, methoxy, formyl, ethoxycarbonyl and dimethylamidocarbonyl.

10. The method of claim 7, wherein $R^3$ is substituted phenyl and each and any of the substituents is individually any independently selected from the group consisting of alkyl, substituted alkyl, alkoxy, substituted alkoxy, alkynyl and halogen.

11. The method of claim 10, wherein
alkyl is methyl or ethyl,
substituted alkyl is halogen-substituted methyl or acetyl,
alkoxy is ethoxy, and
alkenyl is vinyl.

12. The method of claim 7, wherein the compound is of formula (IV)

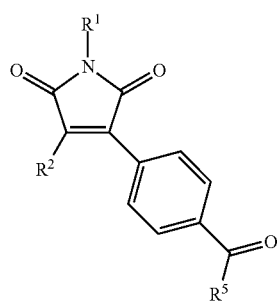

wherein $R^5$ is selected from the group consisting of alkyl, aminoalkyl, alkoxyalkyl, hydroxyalkyl, aryl and heteroaryl.

13. The method of claim 12, wherein
$R^5$ is methyl.

14. The method of claim 1, wherein
$R^2$ is a moiety of formula (VIa)

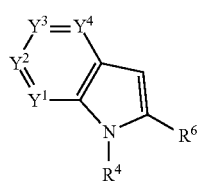

wherein
$R^4$ is selected from the group consisting of hydrogen, aryl, heteroaryl, alkyl, cycloalkyl, polyfluoroalkyl, arylalkyl and heteroarylalkyl,
$R^6$ is selected from the group consisting of alkyl and aryl,
each and any of $Y^1$, $Y^2$, $Y^3$ and $Y^4$ is individually and independently selected from the group consisting of N and $CR^7$, under the proviso that at least two of $Y^1$, $Y^2$, $Y^3$ and $Y^4$ are $CR^7$,
wherein
each and any of $R^7$ is individually and independently selected from the group consisting of hydrogen, halogen, alkyl, alkenyl, alkynyl, acyl, formyl, cycloalkyl, aryl, haloalkyl, polyfluoroalkyl, alkylthio, arylthio, monoalkylamino, dialkylamino, monoarylamino, diarylamino, alkyl aryl amino, alkylimido, hydroxy, alkoxy, aryloxy, carboxyl, alkoxycarbonyl, aryloxycarbonyl, cyano, amino, amido, acylamino, nitro, alkylsulfinyl, arylsulfinyl, alkyl sulfonyl, aryl sulfonyl, alkyl sulfinamido, aryl sulfinamido, alkyl sulfonamido and arylsulfonamido.

15. The method of claim 14, wherein
each and any of $Y^1$, $Y^2$, $Y^3$ and $Y^4$ is $CR^7$.

16. The method of claim 15, wherein
$R^7$ is hydrogen.

17. The method of claim 14, wherein
$R^4$ is selected from the group consisting of hydrogen, alkyl and benzyl, and/or wherein
$R^6$ is hydrogen or alkyl.

18. The method of claim 14, wherein
each and any of $Y^1$, $Y^2$, $Y^3$ and $Y^4$ is individually and independently selected from the group consisting of N and $CR^7$, under the proviso that one or two of $Y^1$, $Y^2$, $Y^3$ and $Y^4$ are N.

19. The method of claim 18, wherein
$R^7$ is hydrogen.

20. The method of claim 14, wherein
$R^4$ is selected from the group consisting of hydrogen, alkyl and benzyl, and/or wherein
$R^6$ is hydrogen or alkyl.

21. The method of claim 14, wherein the compound is of formula (VI)

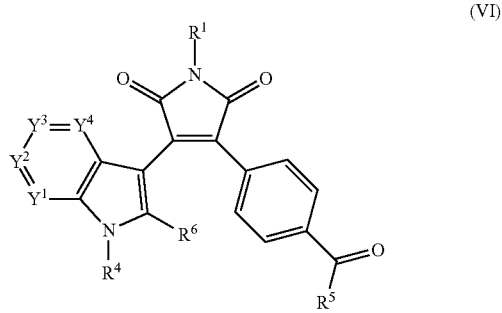

wherein $R^5$ is selected from the group consisting of alkyl, aminoalkyl, alkoxyalkyl, hydroxyalkyl, aryl and heteroaryl, or wherein the compound is of formula (V)

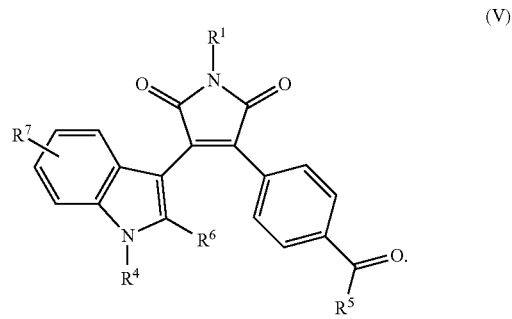

22. The method of claim 21, wherein
$R^5$ is methyl.

23. The method claim 1, wherein the compound is selected from the group consisting of 1-Methyl-3,4-bis-(2-methyl-1H-indol-3-yl)-1H-pyrrole-2,5-dione; 1-Methyl-3-(2-methyl-1H-indol-3-yl)-4-(4-vinylphenyl)-1H-pyrrole-2,5-dione; 1-Methyl-3-(2-methyl-1H-indol-3-yl)-4-phenyl-1H-pyrrole-2,5-dione; 3-(4-Acetylphenyl)-1-methyl-4-(2-methyl-1H-indol-3-yl)-1H-pyrrole-2,5-dione (also referred to herein as PDA-66); 3-(2,6-Dimethylphenyl)-1-methyl-4-(2-methyl-1H-indol-3-yl)-1H-pyrrole-2,5-dione; 3-(3-Chlorophenyl)-1-methyl-4-(2-methyl-1H-indol-3-yl)-1H-pyrrole-2,5-dione; 3-(2,4-Dichlorophenyl)-1-methyl-4-(2-methyl-1H-indol-3-yl)-1H-pyrrole-2,5-dione; 1-Methyl-3-(2-methyl-1H-indol-3-yl)-4-(thiophen-3-yl)-1H-pyrrole-2,5-dione; 1-Methyl-3-(2-methyl-1H-indol-3-yl)-4-(pyridin-4-yl)-1H-pyrrole-2,5-dione; 1-Methyl-3-(2-methyl-1H-indol-3-yl)-4-(naphthalen-2-yl)-1H-pyrrole-2,5-dione; 3-(2,5-Dimethoxyphenyl)-1-methyl-4-(2-methyl-1H-indol-3-yl)-1H-pyrrole-2,5-dione; 1-Methyl-3-(2-methyl-1H-indol-3-yl)-4-(2-(trifluoromethyl)phenyl)-1H-pyrrole-2,5-dione; 3-(4-Fluorophenyl)-1-methyl-4-(2-methyl-1H-indol-3-yl)-1H-pyrrole-2,5-dione; 3-(5-Acetyl-2-fluorophenyl)-1-methyl-4-(2-methyl-1H-indol-3-yl)-1H-pyrrole-2,5-dione; N-(4-(1-Methyl-4-(2-methyl-1H-indol-3-yl)-2, 5-di oxo-2, 5-dihydro-1H-pyrrol-3-yl)phenyl) acetamide; 3-(2-Methyl-1H-indol-3-yl)-4-phenylfuran-2, 5-dione; 3-(4-Acetylphenyl)-4-(2-methyl-1H-indol-3-yl)-1H-pyrrole-2, 5-dione; 3-(2-Methyl-1H-indol-3-yl)-4-(naphthalen-2-yl)furan-2, 5-dione; 3-(2-Methyl-1H-indol-3-yl)-4-(naphthalen-2-yl)-1H-pyrrole-2, 5-dione; 3-(4-Acetylphenyl)-4-(2-methyl-1H-indol-3-yl)furan-2, 5-dione; and 3-(2-Methyl-1H-indol-3-yl)-4-phenyl-1H-pyrrole-2, 5-dione.

24. The method of claim 1, wherein the compound is 3-(4-acetylphenyl)-4-(2-methyl-1H-indol-3-yl)-1H-pyrrole-2,5-dione

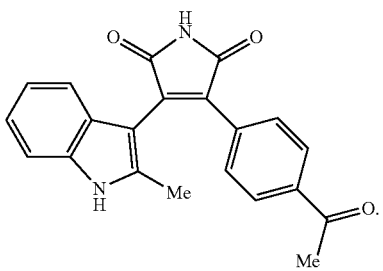

(VII)

25. The method of claim 1, wherein the compound is 3-(4-acetylphenyl)-1-methyl-4-(2-methyl-1H-indol-3-yl)-1H-pyrrole-2,5-dione

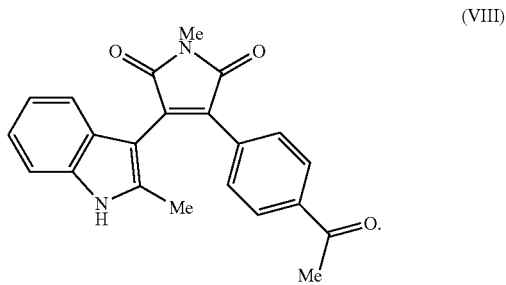 [SMILES: CC(=O)c1ccc(C2=C(c3c(C)[nH]c4ccccc34)C(=O)N(C)C2=O)cc1]

(VIII)

26. The method of claim 1, wherein leukemia is selected from the group consisting of acute lymphoblastic leukemia (ALL), acute myeloid leukemia (AML), refractory leukemia, resistant leukemia, FLT3-ITD-positive leukemia, any chronic leukemia, myelodysplasia, and lymphoma.

27. The method of claim 1, further comprising administering a chemotherapeutic agent.

28. The method of claim 27, wherein the chemotherapeutic agent is selected from the group comprising cytarabine, etoposide, mitoxantron, cyclophosphamide, retinoic acid, daunorubicin, doxorubicin, idarubicin, azacytidine, decitabine, a tyrosine-kinase inhibitor, a antineoplastic antibody, vincaalkaloids and steroids.

29. The method of claim 28, wherein the chemotherapeutic agent is a tyrosine-kinase inhibitor, wherein the tyrosine-kinase inhibitor is selected from the group comprising sorafenib, dasatinib, nilotinib, nelarabine and fludarabine or wherein the chemotherapeutic agent is Alemtuzumab.

* * * * *

UNITED STATES PATENT AND TRADEMARK OFFICE
CERTIFICATE OF CORRECTION

PATENT NO.       : 9,724,331 B2  
APPLICATION NO.  : 14/650939  
DATED            : August 8, 2017  
INVENTOR(S)      : Matthias Beller et al.

Page 1 of 1

It is certified that error appears in the above-identified patent and that said Letters Patent is hereby corrected as shown below:

On the Title Page

(87) PCT Publication Date should be -- June 19, 2014 --.

In the Claims

At Column 44, Line 54-55, please delete ", substituted phenyl, naphthenyl,".

Signed and Sealed this  
Twenty-eighth Day of November, 2017

Joseph Matal  
*Performing the Functions and Duties of the*  
*Under Secretary of Commerce for Intellectual Property and*  
*Director of the United States Patent and Trademark Office*